(12) United States Patent
Ek et al.

(10) Patent No.: US 8,556,902 B2
(45) Date of Patent: Oct. 15, 2013

(54) SYSTEM AND METHOD FOR RETROGRADE PROCEDURE

(75) Inventors: Steven W. Ek, Bolton, MA (US); Tim Brightman, Franklin, MA (US); Anthony Miniaci, Bentleyville, OH (US)

(73) Assignee: Arthrosurface Incorporated, Franklin, MA (US)

( * ) Notice: Subject to any disclaimer, the term of this patent is extended or adjusted under 35 U.S.C. 154(b) by 0 days.

(21) Appl. No.: 13/043,430

(22) Filed: Mar. 8, 2011

(65) Prior Publication Data

US 2011/0196434 A1  Aug. 11, 2011

Related U.S. Application Data

(63) Continuation of application No. 11/209,170, filed on Aug. 22, 2005, now Pat. No. 7,901,408, and a continuation-in-part of application No. 11/169,326, filed on Jun. 28, 2005, now Pat. No. 8,361,159, said application No. 11/209,170 is a continuation-in-part of application No. 10/994,453, filed on Nov. 22, 2004, now Pat. No. 7,896,885, said application No. 11/209,170 is a continuation-in-part of application No. 10/308,718, filed on Dec. 3, 2002, now Pat. No. 7,163,541.

(60) Provisional application No. 60/603,473, filed on Aug. 20, 2004, provisional application No. 60/583,549, filed on Jun. 28, 2004, provisional application No. 60/523,810, filed on Nov. 20, 2003.

(51) Int. Cl.
*A61B 17/56* (2006.01)

(52) U.S. Cl.
USPC .......................................... 606/86 R; 606/89

(58) Field of Classification Search
USPC ............. 606/79, 80–81, 86 R, 88–89, 96–99, 606/103–104
See application file for complete search history.

(56) References Cited

U.S. PATENT DOCUMENTS

| 992,819 A | 5/1911 | Springer |
| 1,451,610 A | 4/1923 | Gestas |

(Continued)

FOREIGN PATENT DOCUMENTS

| AU | 2001262308 | 12/2001 |
| AU | 2001259327 B2 | 2/2005 |

(Continued)

OTHER PUBLICATIONS

Sullivan, "Hallux Rigidus: MTP Implant Arthroplasty," Foot Ankle Clin. N. Am. 14 (2009) pp. 33-42.

(Continued)

*Primary Examiner* — Nicholas Woodall
*Assistant Examiner* — Larry E. Waggle, Jr.
(74) *Attorney, Agent, or Firm* — Grossman Tucker Perreault & Pfleger PLLC

(57) ABSTRACT

A system and method may be used for accessing an articular surface and for preparing an implant site on the articular surface. The method may include locating a portion of the articular. An access passage may be drilled towards the articular surface though bone behind the articular surface. An implant site may be excised in the articular surface relative to an axis defined by the access passage.

19 Claims, 15 Drawing Sheets

(56) References Cited

U.S. PATENT DOCUMENTS

| | | |
|---|---|---|
| 2,267,925 A | 12/1941 | Johnston |
| 2,379,984 A | 7/1943 | Nereaux |
| 2,381,102 A | 10/1943 | Boyd |
| 2,570,465 A | 10/1951 | Lundholm |
| 3,176,395 A | 4/1965 | Warner et al. |
| 3,715,763 A | 2/1973 | Link |
| 3,840,905 A | 10/1974 | Deane |
| 3,852,830 A | 12/1974 | Marmor |
| 4,016,651 A | 4/1977 | Kawahara et al. |
| 4,016,874 A | 4/1977 | Maffei et al. |
| 4,034,418 A | 7/1977 | Jackson et al. |
| 4,044,464 A | 8/1977 | Schiess et al. |
| 4,158,894 A | 6/1979 | Worrell |
| 4,319,577 A | 3/1982 | Bofinger et al. |
| 4,330,891 A | 5/1982 | Brånemark et al. |
| 4,340,978 A | 7/1982 | Buechel et al. |
| 4,344,192 A | 8/1982 | Imbert |
| 4,433,687 A | 2/1984 | Burke et al. |
| 4,462,120 A | 7/1984 | Rambert et al. |
| 4,474,177 A | 10/1984 | Whiteside |
| 4,484,570 A | 11/1984 | Sutter et al. |
| 4,531,517 A | 7/1985 | Forte et al. |
| 4,535,768 A | 8/1985 | Hourahane et al. |
| 4,565,768 A | 1/1986 | Nonogaki et al. |
| 4,634,720 A | 1/1987 | Dorman et al. |
| 4,655,752 A | 4/1987 | Honkanen et al. |
| 4,661,536 A | 4/1987 | Dorman et al. |
| 4,662,371 A | 5/1987 | Whipple et al. |
| 4,664,669 A | 5/1987 | Ohyabu et al. |
| 4,673,407 A | 6/1987 | Martin |
| 4,693,986 A | 9/1987 | Vit et al. |
| 4,708,139 A | 11/1987 | Dunbar, IV |
| 4,712,545 A | 12/1987 | Honkanen |
| 4,714,478 A | 12/1987 | Fischer |
| 4,719,908 A | 1/1988 | Averill et al. |
| 4,722,331 A | 2/1988 | Fox |
| 4,729,761 A | 3/1988 | White |
| 4,781,182 A | 11/1988 | Purnell et al. |
| 4,788,970 A | 12/1988 | Karas et al. |
| 4,823,780 A | 4/1989 | Odensten et al. |
| 4,842,604 A | 6/1989 | Dorman et al. |
| 4,896,663 A | 1/1990 | Vandewalls |
| 4,911,153 A | 3/1990 | Border |
| 4,911,720 A | 3/1990 | Collier |
| 4,920,958 A | 5/1990 | Walt et al. |
| 4,927,421 A | 5/1990 | Goble et al. |
| 4,936,853 A | 6/1990 | Fabian et al. |
| 4,938,778 A | 7/1990 | Ohyabu et al. |
| 4,940,467 A | 7/1990 | Tronzo |
| 4,945,904 A | 8/1990 | Bolton et al. |
| 4,976,037 A | 12/1990 | Hines |
| 4,978,258 A | 12/1990 | Lins |
| 4,979,957 A | 12/1990 | Hodorek |
| 4,989,110 A | 1/1991 | Zevin et al. |
| 4,990,163 A | 2/1991 | Ducheyne et al. |
| 4,997,434 A | 3/1991 | Seedhom et al. |
| 4,998,938 A | 3/1991 | Ghajar et al. |
| 5,007,930 A | 4/1991 | Dorman et al. |
| 5,019,104 A | 5/1991 | Whiteside et al. |
| 5,053,049 A | 10/1991 | Campbell |
| 5,092,895 A | 3/1992 | Albrektsson et al. |
| 5,100,405 A | 3/1992 | McLaren |
| 5,127,920 A | 7/1992 | MacArthur |
| 5,154,720 A | 10/1992 | Trott et al. |
| 5,180,384 A | 1/1993 | Mikhail |
| 5,192,291 A | 3/1993 | Pannek, Jr. |
| 5,201,881 A | 4/1993 | Evans |
| 5,207,753 A | 5/1993 | Badrinath |
| 5,211,647 A | 5/1993 | Schmieding |
| 5,224,945 A | 7/1993 | Pannek, Jr. |
| 5,234,435 A | 8/1993 | Seagrave, Jr. |
| 5,255,838 A | 10/1993 | Gladdish, Jr. et al. |
| 5,263,498 A | 11/1993 | Caspari et al. |
| 5,263,987 A | 11/1993 | Shah |
| 5,282,863 A | 2/1994 | Burton |
| 5,290,313 A | 3/1994 | Heldreth |
| 5,312,411 A | 5/1994 | Steele |
| 5,314,478 A | 5/1994 | Oka et al. |
| 5,314,482 A | 5/1994 | Goodfellow et al. |
| 5,324,295 A | 6/1994 | Shapiro |
| 5,336,224 A | 8/1994 | Selman |
| 5,354,300 A | 10/1994 | Goble et al. |
| 5,358,525 A | 10/1994 | Fox et al. |
| 5,360,446 A | 11/1994 | Kennedy |
| 5,374,270 A | 12/1994 | McGuire et al. |
| 5,383,937 A | 1/1995 | Mikhail |
| 5,387,218 A | 2/1995 | Meswania |
| 5,395,401 A | 3/1995 | Bahler |
| 5,409,490 A | 4/1995 | Ethridge |
| 5,409,494 A | 4/1995 | Morgan |
| 5,413,608 A | 5/1995 | Keller |
| 5,423,822 A | 6/1995 | Hershberger |
| 5,423,823 A | 6/1995 | Schmieding |
| 5,425,733 A | 6/1995 | Schmieding |
| 5,458,643 A | 10/1995 | Oka et al. |
| 5,480,443 A | 1/1996 | Elias |
| 5,486,178 A | 1/1996 | Hodge |
| 5,509,918 A | 4/1996 | Romano |
| 5,520,695 A | 5/1996 | Luckman |
| 5,522,900 A | 6/1996 | Hollister |
| 5,534,031 A | 7/1996 | Matsuzaki et al. |
| 5,540,696 A | 7/1996 | Booth, Jr. et al. |
| 5,562,664 A | 10/1996 | Durlacher et al. |
| 5,580,353 A | 12/1996 | Mendes et al. |
| 5,591,170 A | 1/1997 | Spievack et al. |
| 5,593,450 A | 1/1997 | Scott et al. |
| 5,595,193 A | 1/1997 | Walus et al. |
| 5,597,273 A | 1/1997 | Hirsch |
| 5,601,550 A | 2/1997 | Esser |
| 5,607,480 A | 3/1997 | Beaty |
| 5,616,146 A | 4/1997 | Murray |
| 5,620,055 A | 4/1997 | Javerlhac |
| 5,624,463 A | 4/1997 | Stone et al. |
| 5,632,745 A | 5/1997 | Schwartz |
| 5,634,927 A | 6/1997 | Houston et al. |
| 5,645,598 A | 7/1997 | Brosnahan, III |
| 5,681,311 A | 10/1997 | Foley et al. |
| 5,681,320 A | 10/1997 | McGuire |
| 5,682,886 A | 11/1997 | Delp et al. |
| 5,683,400 A | 11/1997 | McGuire |
| 5,683,465 A | 11/1997 | Shinn et al. |
| 5,683,466 A | 11/1997 | Vitale |
| 5,700,264 A | 12/1997 | Zucherman et al. |
| 5,700,265 A | 12/1997 | Romano |
| 5,702,401 A | 12/1997 | Shaffer |
| 5,702,465 A | 12/1997 | Burkinshaw |
| 5,702,467 A | 12/1997 | Gabriel et al. |
| 5,741,266 A | 4/1998 | Moran et al. |
| 5,765,973 A | 6/1998 | Hirsch et al. |
| 5,769,855 A | 6/1998 | Bertin et al. |
| 5,769,899 A | 6/1998 | Schwartz et al. |
| 5,771,310 A | 6/1998 | Vannah |
| 5,776,137 A | 7/1998 | Katz |
| 5,782,835 A | 7/1998 | Hart et al. |
| 5,800,440 A | 9/1998 | Stead |
| 5,810,851 A | 9/1998 | Yoon |
| 5,816,811 A | 10/1998 | Beaty |
| 5,817,095 A | 10/1998 | Smith |
| 5,824,087 A | 10/1998 | Aspden et al. |
| 5,824,105 A | 10/1998 | Ries et al. |
| RE36,020 E | 12/1998 | Moore et al. |
| 5,882,350 A | 3/1999 | Ralph et al. |
| 5,885,297 A | 3/1999 | Matsen, III |
| 5,885,298 A | 3/1999 | Herrington et al. |
| 5,888,210 A | 3/1999 | Draenert |
| 5,893,889 A | 4/1999 | Harrington |
| 5,895,390 A | 4/1999 | Moran et al. |
| 5,911,126 A | 6/1999 | Massen |
| 5,918,604 A | 7/1999 | Whelan |
| 5,919,196 A | 7/1999 | Bobic et al. |
| 5,928,239 A | 7/1999 | Mirza |
| 5,928,241 A | 7/1999 | Menut et al. |
| 5,928,286 A | 7/1999 | Ashby et al. |
| 5,964,752 A | 10/1999 | Stone |

(56) References Cited

U.S. PATENT DOCUMENTS

| | | |
|---|---|---|
| 5,964,768 A | 10/1999 | Huebner |
| 5,964,808 A | 10/1999 | Blaha et al. |
| 5,968,050 A | 10/1999 | Torrie |
| 5,989,269 A | 11/1999 | Vibe-Hansen et al. |
| 5,990,382 A | 11/1999 | Fox |
| 5,997,543 A | 12/1999 | Truscott |
| 5,997,582 A | 12/1999 | Weiss |
| 6,004,323 A | 12/1999 | Park et al. |
| 6,010,502 A | 1/2000 | Bagby |
| 6,015,411 A | 1/2000 | Ohkoshi et al. |
| 6,017,348 A | 1/2000 | Hart et al. |
| 6,019,767 A | 2/2000 | Howell |
| 6,019,790 A | 2/2000 | Holmberg et al. |
| 6,045,564 A | 4/2000 | Walen |
| 6,052,909 A | 4/2000 | Gardner |
| 6,059,831 A | 5/2000 | Braslow |
| 6,071,310 A | 6/2000 | Picha et al. |
| 6,081,741 A | 6/2000 | Hollis |
| 6,086,593 A | 7/2000 | Bonutti |
| 6,086,614 A | 7/2000 | Mumme |
| 6,102,948 A | 8/2000 | Brosnahan, III |
| 6,120,511 A | 9/2000 | Chan |
| 6,120,542 A | 9/2000 | Camino et al. |
| 6,132,433 A | 10/2000 | Whelan |
| 6,146,385 A | 11/2000 | Torrie et al. |
| 6,149,654 A | 11/2000 | Johnson |
| 6,152,960 A | 11/2000 | Pappas |
| 6,159,216 A | 12/2000 | Burkinshaw et al. |
| 6,165,223 A | 12/2000 | Metzger et al. |
| 6,168,626 B1 | 1/2001 | Hyon et al. |
| 6,171,340 B1 | 1/2001 | McDowell |
| 6,193,724 B1 | 2/2001 | Chan |
| 6,206,885 B1 | 3/2001 | Ghahremani et al. |
| 6,206,926 B1 | 3/2001 | Pappas |
| 6,217,549 B1 | 4/2001 | Selmon et al. |
| 6,217,619 B1 | 4/2001 | Keller |
| 6,235,060 B1 | 5/2001 | Kubein-Meesenburg et al. |
| 6,251,143 B1 | 6/2001 | Schwartz et al. |
| 6,254,605 B1 | 7/2001 | Howell |
| 6,270,347 B1 | 8/2001 | Webster et al. |
| 6,280,474 B1 | 8/2001 | Cassidy et al. |
| 6,299,645 B1 | 10/2001 | Ogden |
| 6,299,648 B1 | 10/2001 | Doubler et al. |
| 6,306,142 B1 | 10/2001 | Johanson et al. |
| 6,315,798 B1 | 11/2001 | Ashby et al. |
| 6,322,500 B1 | 11/2001 | Sikora et al. |
| 6,328,752 B1 | 12/2001 | Sjostrom et al. |
| 6,342,075 B1 | 1/2002 | MacArthur |
| 6,358,251 B1 | 3/2002 | Mirza |
| 6,358,253 B1 | 3/2002 | Torrie et al. |
| 6,364,910 B1 | 4/2002 | Shultz et al. |
| 6,375,658 B1 | 4/2002 | Hangody et al. |
| 6,383,188 B2 | 5/2002 | Kuslich |
| 6,415,516 B1 | 7/2002 | Tirado et al. |
| 6,443,954 B1 | 9/2002 | Bramlet et al. |
| 6,451,023 B1 | 9/2002 | Salazar et al. |
| 6,461,373 B2 | 10/2002 | Wyman et al. |
| 6,468,309 B1 | 10/2002 | Lieberman |
| 6,478,801 B1 | 11/2002 | Ralph et al. |
| 6,478,822 B1 | 11/2002 | Leroux et al. |
| 6,482,210 B1 | 11/2002 | Skiba et al. |
| 6,494,914 B2 | 12/2002 | Brown |
| 6,520,964 B2 | 2/2003 | Tallarida et al. |
| 6,527,754 B1 | 3/2003 | Tallarida et al. |
| 6,530,956 B1 | 3/2003 | Mansmann |
| 6,540,786 B2 | 4/2003 | Chibrac et al. |
| 6,551,322 B1 | 4/2003 | Lieberman |
| 6,554,866 B1 | 4/2003 | Aicher et al. |
| 6,575,980 B1 | 6/2003 | Robie et al. |
| 6,575,982 B1 | 6/2003 | Bonutti |
| 6,585,666 B2 | 7/2003 | Suh et al. |
| 6,591,581 B2 | 7/2003 | Schmieding |
| 6,599,321 B2 | 7/2003 | Hyde et al. |
| 6,602,258 B1 | 8/2003 | Katz |
| 6,607,561 B2 | 8/2003 | Brannon |
| 6,610,067 B2 | 8/2003 | Tallarida |
| 6,610,095 B1 | 8/2003 | Pope et al. |
| 6,623,474 B1 | 9/2003 | Ponzi |
| 6,626,950 B2 | 9/2003 | Brown et al. |
| 6,629,997 B2 | 10/2003 | Mansmann |
| 6,632,246 B1 | 10/2003 | Simon et al. |
| 6,679,917 B2 | 1/2004 | Ek |
| 6,746,451 B2 | 6/2004 | Middleton et al. |
| 6,755,837 B2 | 6/2004 | Ebner |
| 6,755,865 B2 | 6/2004 | Tarabishy |
| 6,770,078 B2 | 8/2004 | Bonutti |
| 6,783,550 B2 | 8/2004 | MacArthur |
| 6,783,551 B1 | 8/2004 | Metzger |
| 6,802,864 B2 | 10/2004 | Tornier |
| 6,814,735 B1 | 11/2004 | Zirngibl |
| 6,827,722 B1 | 12/2004 | Schoenefeld |
| 6,860,902 B2 | 3/2005 | Reiley |
| 6,884,246 B1 | 4/2005 | Sonnabend et al. |
| 6,884,621 B2 | 4/2005 | Liao et al. |
| 6,893,467 B1 | 5/2005 | Bercovy |
| 6,923,813 B2 | 8/2005 | Phillips et al. |
| 6,926,739 B1 | 8/2005 | OConnor |
| 6,962,577 B2 | 11/2005 | Tallarida et al. |
| 6,969,393 B2 | 11/2005 | Pinczewski et al. |
| 6,984,248 B2 | 1/2006 | Hyde, Jr. |
| 6,989,016 B2 | 1/2006 | Tallarida et al. |
| 7,029,479 B2 | 4/2006 | Tallarida |
| 7,048,767 B2 | 5/2006 | Namavar |
| 7,063,717 B2 | 6/2006 | St. Pierre et al. |
| 7,112,205 B2 | 9/2006 | Carrison |
| 7,115,131 B2 | 10/2006 | Engh et al. |
| 7,118,578 B2 | 10/2006 | West, Jr. et al. |
| 7,156,880 B2 | 1/2007 | Evans et al. |
| 7,160,305 B2 | 1/2007 | Schmieding |
| 7,163,541 B2 | 1/2007 | Ek |
| 7,166,133 B2 | 1/2007 | Evans et al. |
| 7,192,431 B2 | 3/2007 | Hangody et al. |
| 7,192,432 B2 | 3/2007 | Wetzler et al. |
| 7,204,839 B2 | 4/2007 | Dreyfuss et al. |
| 7,204,854 B2 | 4/2007 | Guederian et al. |
| 7,235,107 B2 | 6/2007 | Evans et al. |
| 7,238,189 B2 | 7/2007 | Schmieding et al. |
| 7,241,316 B2 | 7/2007 | Evans et al. |
| 7,264,634 B2 | 9/2007 | Schmieding |
| 7,290,347 B2 | 11/2007 | Augostino et al. |
| 7,303,577 B1 | 12/2007 | Dean |
| 7,311,702 B2 | 12/2007 | Tallarida et al. |
| 7,361,195 B2 | 4/2008 | Schwartz et al. |
| 7,368,065 B2 | 5/2008 | Yang et al. |
| 7,371,260 B2 | 5/2008 | Malinin |
| 7,462,199 B2 | 12/2008 | Justin et al. |
| 7,468,075 B2 | 12/2008 | Lang et al. |
| 7,476,250 B1 | 1/2009 | Mansmann |
| 7,491,235 B2 | 2/2009 | Fell |
| 7,501,073 B2 | 3/2009 | Wen et al. |
| 7,510,558 B2 | 3/2009 | Tallarida |
| 7,531,000 B2 | 5/2009 | Hodorek |
| 7,559,932 B2 | 7/2009 | Truckai et al. |
| 7,569,059 B2 | 8/2009 | Cerundolo |
| 7,572,291 B2 | 8/2009 | Gil et al. |
| 7,575,578 B2 | 8/2009 | Wetzler et al. |
| 7,578,824 B2 | 8/2009 | Justin et al. |
| 7,604,641 B2 | 10/2009 | Tallarida et al. |
| 7,611,653 B1 | 11/2009 | Elsner et al. |
| 7,618,451 B2 | 11/2009 | Berez et al. |
| 7,618,462 B2 | 11/2009 | Ek |
| 7,632,294 B2 | 12/2009 | Milbodker et al. |
| 7,641,658 B2 | 1/2010 | Shaolian et al. |
| 7,641,689 B2 | 1/2010 | Fell et al. |
| 7,670,381 B2 | 3/2010 | Schwartz |
| 7,678,151 B2 | 3/2010 | Ek |
| 7,682,540 B2 | 3/2010 | Boyan et al. |
| 7,687,462 B2 | 3/2010 | Ting et al. |
| 7,708,741 B1 | 5/2010 | Bonutti |
| 7,713,305 B2 | 5/2010 | Ek |
| 7,722,676 B2 | 5/2010 | Hanson et al. |
| 7,731,720 B2 | 6/2010 | Sand et al. |
| 7,758,643 B2 | 7/2010 | Stone et al. |
| 7,806,872 B2 | 10/2010 | Ponzi |

(56) References Cited

U.S. PATENT DOCUMENTS

| | | | |
|---|---|---|---|
| 7,815,645 B2 | 10/2010 | Haines |
| 7,828,853 B2 | 11/2010 | Ek et al. |
| 7,842,042 B2 | 11/2010 | Reay-Young et al. |
| 7,857,817 B2 | 12/2010 | Tallarida et al. |
| 7,896,883 B2 | 3/2011 | Ek et al. |
| 7,896,885 B2 | 3/2011 | Miniaci et al. |
| 7,901,408 B2 | 3/2011 | Ek et al. |
| 7,914,545 B2 | 3/2011 | Ek |
| 7,931,683 B2 | 4/2011 | Weber et al. |
| 7,951,163 B2 | 5/2011 | Ek |
| 7,955,382 B2 | 6/2011 | Flanagan et al. |
| 7,959,636 B2 | 6/2011 | Schmieding |
| 7,967,823 B2 | 6/2011 | Ammann et al. |
| 7,993,360 B2 | 8/2011 | Hacker et al. |
| 7,993,369 B2 | 8/2011 | Dreyfuss |
| 7,998,206 B2 | 8/2011 | Shepard |
| 8,012,206 B2 | 9/2011 | Schmieding |
| 8,021,367 B2 | 9/2011 | Bourke et al. |
| 8,038,652 B2 | 10/2011 | Morrison et al. |
| 8,038,678 B2 | 10/2011 | Schmieding et al. |
| 8,043,315 B2 | 10/2011 | Shepard |
| 8,043,319 B2 | 10/2011 | Lyon et al. |
| 8,048,079 B2 | 11/2011 | Iannarone |
| 8,048,157 B2 | 11/2011 | Albertorio |
| 8,057,478 B2 | 11/2011 | Kuczynski et al. |
| 8,062,301 B2 | 11/2011 | Ammann et al. |
| 8,062,319 B2 | 11/2011 | O'Quinn et al. |
| 8,083,746 B2 | 12/2011 | Novak |
| 8,083,749 B2 | 12/2011 | Taber |
| 8,083,803 B2 | 12/2011 | Albertorio et al. |
| 8,097,040 B2 | 1/2012 | Russo et al. |
| 8,137,406 B2 | 3/2012 | Novak et al. |
| 8,142,502 B2 | 3/2012 | Stone et al. |
| 8,147,559 B2 | 4/2012 | Tallarida et al. |
| 8,152,847 B2 | 4/2012 | Strzepa et al. |
| 8,162,947 B2 | 4/2012 | Dreyfuss |
| 8,167,951 B2 | 5/2012 | Ammann et al. |
| 8,177,738 B2 | 5/2012 | Schmieding et al. |
| 8,177,841 B2 | 5/2012 | Ek |
| 8,182,489 B2 | 5/2012 | Horacek |
| 8,202,282 B2 | 6/2012 | Schmieding et al. |
| 8,202,296 B2 | 6/2012 | Burkhart |
| 8,202,297 B2 | 6/2012 | Burkhart |
| 8,202,298 B2 | 6/2012 | Cook et al. |
| 8,202,306 B2 | 6/2012 | Dreyfuss |
| 8,202,318 B2 | 6/2012 | Willobee |
| 8,211,112 B2 | 7/2012 | Novak et al. |
| 8,221,455 B2 | 7/2012 | Shurnas et al. |
| 8,231,653 B2 | 7/2012 | Dreyfuss |
| 8,231,674 B2 | 7/2012 | Albertorio et al. |
| 8,236,000 B2 | 8/2012 | Ammann et al. |
| 8,298,247 B2 | 10/2012 | Sterrett et al. |
| 8,298,284 B2 | 10/2012 | Cassani |
| 8,308,662 B2 | 11/2012 | Lo |
| 8,308,732 B2 | 11/2012 | Millett et al. |
| 8,323,347 B2 | 12/2012 | Guederian et al. |
| 8,328,716 B2 | 12/2012 | Schmieding et al. |
| 8,333,774 B2 | 12/2012 | Morrison |
| 8,343,186 B2 | 1/2013 | Dreyfuss et al. |
| 8,348,960 B2 | 1/2013 | Michel et al. |
| 8,348,975 B2 | 1/2013 | Dreyfuss |
| 8,353,915 B2 | 1/2013 | Helenbolt et al. |
| 8,361,159 B2 | 1/2013 | Ek |
| 8,377,068 B2 | 2/2013 | Aker et al. |
| 8,382,789 B2 | 2/2013 | Weber et al. |
| 8,382,810 B2 | 2/2013 | Peterson et al. |
| 8,388,624 B2 | 3/2013 | Ek et al. |
| 8,398,678 B2 | 3/2013 | Baker et al. |
| 8,409,209 B2 | 4/2013 | Ammann et al. |
| 8,409,250 B2 | 4/2013 | Schmieding et al. |
| 8,419,794 B2 | 4/2013 | ElAttrache et al. |
| 8,425,554 B2 | 4/2013 | Denove et al. |
| 8,430,909 B2 | 4/2013 | Dreyfuss |
| 8,435,272 B2 | 5/2013 | Dougherty et al. |
| 8,439,976 B2 | 5/2013 | Albertorio et al. |
| 8,444,680 B2 | 5/2013 | Dooney, Jr. et al. |
| 8,460,317 B2 | 6/2013 | Merves |
| 8,460,318 B2 | 6/2013 | Murray et al. |
| 8,460,350 B2 | 6/2013 | Albertorio et al. |
| 8,460,379 B2 | 6/2013 | Albertorio et al. |
| 2001/0010023 A1 | 7/2001 | Schwartz et al. |
| 2001/0012967 A1* | 8/2001 | Mosseri ............... 623/23.12 |
| 2001/0034526 A1 | 10/2001 | Kuslich et al. |
| 2001/0039455 A1 | 11/2001 | Simon et al. |
| 2001/0053914 A1 | 12/2001 | Landry et al. |
| 2001/0056266 A1 | 12/2001 | Tallarida et al. |
| 2002/0022847 A1 | 2/2002 | Ray, III et al. |
| 2002/0022889 A1 | 2/2002 | Chibrac et al. |
| 2002/0049444 A1 | 4/2002 | Knox |
| 2002/0055783 A1 | 5/2002 | Tallarida et al. |
| 2002/0106393 A1 | 8/2002 | Bianchi et al. |
| 2002/0138150 A1 | 9/2002 | Leclercq |
| 2002/0143342 A1 | 10/2002 | Hangody et al. |
| 2002/0147498 A1 | 10/2002 | Tallarida et al. |
| 2002/0155144 A1 | 10/2002 | Troczynski et al. |
| 2002/0156480 A1 | 10/2002 | Overes et al. |
| 2002/0173797 A1 | 11/2002 | Van Zile et al. |
| 2003/0028196 A1 | 2/2003 | Bonutti |
| 2003/0060887 A1 | 3/2003 | Ek |
| 2003/0065391 A1* | 4/2003 | Re et al. ............... 623/13.14 |
| 2003/0100953 A1 | 5/2003 | Rosa et al. |
| 2003/0105465 A1 | 6/2003 | Schmieding et al. |
| 2003/0120276 A1 | 6/2003 | Tallarida et al. |
| 2003/0120278 A1 | 6/2003 | Morgan et al. |
| 2003/0130741 A1 | 7/2003 | McMinn |
| 2003/0144736 A1 | 7/2003 | Sennett |
| 2003/0171756 A1 | 9/2003 | Fallin et al. |
| 2003/0181878 A1 | 9/2003 | Tallarida et al. |
| 2003/0195470 A1 | 10/2003 | Ponzi |
| 2003/0204195 A1 | 10/2003 | Keane et al. |
| 2003/0204267 A1 | 10/2003 | Hazebrouck et al. |
| 2003/0216669 A1 | 11/2003 | Lang et al. |
| 2003/0216742 A1 | 11/2003 | Wetzler et al. |
| 2003/0225456 A1 | 12/2003 | Ek |
| 2003/0225457 A1 | 12/2003 | Justin et al. |
| 2003/0229352 A1 | 12/2003 | Penenberg |
| 2004/0015170 A1 | 1/2004 | Tallarida et al. |
| 2004/0033212 A1 | 2/2004 | Thomson et al. |
| 2004/0034359 A1 | 2/2004 | Schmieding et al. |
| 2004/0034437 A1 | 2/2004 | Schmieding |
| 2004/0039389 A1 | 2/2004 | West, Jr. et al. |
| 2004/0082906 A1 | 4/2004 | Tallarida et al. |
| 2004/0092946 A1 | 5/2004 | Bagga et al. |
| 2004/0106928 A1 | 6/2004 | Ek |
| 2004/0133276 A1 | 7/2004 | Lang et al. |
| 2004/0138754 A1 | 7/2004 | Lang et al. |
| 2004/0138758 A1 | 7/2004 | Evans et al. |
| 2004/0148030 A1 | 7/2004 | Ek |
| 2004/0153087 A1 | 8/2004 | Sanford et al. |
| 2004/0167632 A1 | 8/2004 | Wen et al. |
| 2004/0167633 A1 | 8/2004 | Wen et al. |
| 2004/0176775 A1 | 9/2004 | Burkus et al. |
| 2004/0193172 A1 | 9/2004 | Ross et al. |
| 2004/0193267 A1 | 9/2004 | Jones et al. |
| 2004/0193268 A1 | 9/2004 | Hazebrouck |
| 2004/0193281 A1 | 9/2004 | Grimes |
| 2004/0199166 A1 | 10/2004 | Schmieding et al. |
| 2004/0204760 A1 | 10/2004 | Fitz et al. |
| 2004/0210309 A1 | 10/2004 | Denzer et al. |
| 2004/0220574 A1 | 11/2004 | Pelo et al. |
| 2004/0230315 A1 | 11/2004 | Ek |
| 2004/0260303 A1 | 12/2004 | Carrison |
| 2005/0015153 A1 | 1/2005 | Goble et al. |
| 2005/0038520 A1 | 2/2005 | Binette et al. |
| 2005/0043805 A1 | 2/2005 | Chudik |
| 2005/0043808 A1 | 2/2005 | Felt et al. |
| 2005/0065612 A1 | 3/2005 | Winslow |
| 2005/0075642 A1 | 4/2005 | Felt |
| 2005/0143731 A1 | 6/2005 | Justin et al. |
| 2005/0143745 A1 | 6/2005 | Hodorek et al. |
| 2005/0143831 A1 | 6/2005 | Justin et al. |
| 2005/0149044 A1 | 7/2005 | Justin et al. |
| 2005/0154398 A1 | 7/2005 | Miniaci et al. |
| 2005/0177171 A1 | 8/2005 | Wetzler et al. |

(56) References Cited

U.S. PATENT DOCUMENTS

| | | |
|---|---|---|
| 2005/0209705 A1 | 9/2005 | Niederauer et al. |
| 2005/0222687 A1 | 10/2005 | Vunjak-Novakovic et al. |
| 2005/0229323 A1 | 10/2005 | Mills et al. |
| 2005/0251268 A1 | 11/2005 | Truncale |
| 2005/0287187 A1 | 12/2005 | Mansmann |
| 2006/0004461 A1 | 1/2006 | Justin et al. |
| 2006/0009774 A1 | 1/2006 | Goble et al. |
| 2006/0020343 A1 | 1/2006 | Ek |
| 2006/0052878 A1 | 3/2006 | Schmieding |
| 2006/0058744 A1 | 3/2006 | Tallarida et al. |
| 2006/0058809 A1 | 3/2006 | Zink et al. |
| 2006/0058883 A1 | 3/2006 | Aram et al. |
| 2006/0069394 A1 | 3/2006 | Weiler et al. |
| 2006/0074430 A1 | 4/2006 | Deffenbaugh et al. |
| 2006/0085006 A1 | 4/2006 | Ek |
| 2006/0085077 A1 | 4/2006 | Cook et al. |
| 2006/0149370 A1 | 7/2006 | Schmieding et al. |
| 2006/0167560 A1 | 7/2006 | Heck et al. |
| 2006/0184187 A1 | 8/2006 | Surti |
| 2006/0190002 A1 | 8/2006 | Tallarida |
| 2006/0195112 A1 | 8/2006 | Ek |
| 2006/0229726 A1 | 10/2006 | Ek |
| 2006/0271059 A1 | 11/2006 | Reay-Young et al. |
| 2007/0005143 A1 | 1/2007 | Ek |
| 2007/0038302 A1 | 2/2007 | Shultz et al. |
| 2007/0038307 A1 | 2/2007 | Webster et al. |
| 2007/0073394 A1 | 3/2007 | Seedhom et al. |
| 2007/0093842 A1 | 4/2007 | Schmieding |
| 2007/0093848 A1 | 4/2007 | Harris et al. |
| 2007/0093890 A1 | 4/2007 | Eliasen et al. |
| 2007/0093896 A1 | 4/2007 | Malinin |
| 2007/0118136 A1 | 5/2007 | Ek |
| 2007/0118224 A1 | 5/2007 | Shah et al. |
| 2007/0123921 A1 | 5/2007 | Ek |
| 2007/0134291 A1 | 6/2007 | Ting et al. |
| 2007/0179608 A1 | 8/2007 | Ek |
| 2007/0233128 A1 | 10/2007 | Schmieding et al. |
| 2007/0244484 A1 | 10/2007 | Luginbuehl |
| 2007/0250067 A1 | 10/2007 | Schmieding et al. |
| 2007/0255399 A1 | 11/2007 | Eliasen et al. |
| 2007/0255412 A1 | 11/2007 | Hajaj et al. |
| 2007/0265700 A1 | 11/2007 | Eliasen et al. |
| 2007/0270873 A1 | 11/2007 | Flickinger et al. |
| 2007/0282455 A1 | 12/2007 | Luginbuehl et al. |
| 2007/0288031 A1 | 12/2007 | Dreyfuss et al. |
| 2007/0299519 A1 | 12/2007 | Schmieding |
| 2008/0004659 A1 | 1/2008 | Burkhart et al. |
| 2008/0015709 A1 | 1/2008 | Evans et al. |
| 2008/0027430 A1 | 1/2008 | Montgomery et al. |
| 2008/0033443 A1 | 2/2008 | Sikora et al. |
| 2008/0033447 A1 | 2/2008 | Sand |
| 2008/0046084 A1 | 2/2008 | Sledge |
| 2008/0086139 A1 | 4/2008 | Bourke et al. |
| 2008/0097618 A1 | 4/2008 | Baker et al. |
| 2008/0103506 A1 | 5/2008 | Volpi et al. |
| 2008/0154271 A1 | 6/2008 | Berberich et al. |
| 2008/0172125 A1 | 7/2008 | Ek |
| 2008/0183290 A1 | 7/2008 | Baird et al. |
| 2008/0188935 A1 | 8/2008 | Saylor et al. |
| 2008/0195113 A1 | 8/2008 | Sikora |
| 2008/0208201 A1 | 8/2008 | Moindreau et al. |
| 2008/0262625 A1 | 10/2008 | Spriano et al. |
| 2008/0275512 A1 | 11/2008 | Albertorio et al. |
| 2008/0306483 A1 | 12/2008 | Iannarone |
| 2008/0317807 A1 | 12/2008 | Lu et al. |
| 2009/0018543 A1 | 1/2009 | Ammann et al. |
| 2009/0054899 A1 | 2/2009 | Ammann et al. |
| 2009/0069816 A1 | 3/2009 | Sasing et al. |
| 2009/0076512 A1 | 3/2009 | Ammann et al. |
| 2009/0112211 A1 | 4/2009 | Johnstone |
| 2009/0138077 A1 | 5/2009 | Weber et al. |
| 2009/0143783 A1 | 6/2009 | Dower |
| 2009/0143784 A1 | 6/2009 | Petersen et al. |
| 2009/0149860 A1 | 6/2009 | Scribner et al. |
| 2009/0198288 A1 | 8/2009 | Hoof et al. |
| 2009/0210057 A1 | 8/2009 | Liao et al. |
| 2009/0216285 A1 | 8/2009 | Ek et al. |
| 2009/0222012 A1 | 9/2009 | Karnes et al. |
| 2009/0228105 A1 | 9/2009 | Son et al. |
| 2009/0234452 A1 | 9/2009 | Steiner et al. |
| 2009/0264889 A1 | 10/2009 | Long et al. |
| 2009/0264928 A1 | 10/2009 | Blain |
| 2009/0275950 A1 | 11/2009 | Sterrett et al. |
| 2009/0276052 A1 | 11/2009 | Regala et al. |
| 2010/0003638 A1 | 1/2010 | Collins et al. |
| 2010/0015244 A1 | 1/2010 | Jain et al. |
| 2010/0028387 A1 | 2/2010 | Balasundaram et al. |
| 2010/0028999 A1 | 2/2010 | Nain |
| 2010/0036381 A1 | 2/2010 | Vanleeuwen et al. |
| 2010/0092535 A1 | 4/2010 | Cook et al. |
| 2010/0112519 A1 | 5/2010 | Hall et al. |
| 2010/0249930 A1 | 9/2010 | Myers |
| 2010/0256645 A1 | 10/2010 | Zajac et al. |
| 2010/0256758 A1 | 10/2010 | Gordon et al. |
| 2010/0268227 A1 | 10/2010 | Tong et al. |
| 2010/0268346 A1 | 10/2010 | Tong et al. |
| 2011/0009964 A1 | 1/2011 | Schwartz et al. |
| 2011/0059312 A1 | 3/2011 | Howling et al. |
| 2011/0066242 A1 | 3/2011 | Lu et al. |
| 2011/0106271 A1 | 5/2011 | Regala et al. |
| 2011/0125263 A1 | 5/2011 | Webster et al. |
| 2011/0152869 A1 | 6/2011 | Ek et al. |
| 2011/0196367 A1 | 8/2011 | Gallo |
| 2011/0238069 A1 | 9/2011 | Zajac et al. |
| 2011/0251621 A1 | 10/2011 | Sluss et al. |
| 2011/0257753 A1 | 10/2011 | Gordon et al. |
| 2011/0300186 A1 | 12/2011 | Hellstrom et al. |
| 2011/0301716 A1 | 12/2011 | Sirivisoot et al. |
| 2012/0027837 A1 | 2/2012 | DeMuth et al. |
| 2012/0109136 A1 | 5/2012 | Bourque et al. |
| 2012/0116502 A1 | 5/2012 | Su et al. |
| 2012/0123474 A1 | 5/2012 | Zajac et al. |
| 2012/0123541 A1 | 5/2012 | Albertorio et al. |
| 2012/0150225 A1 | 6/2012 | Burkhart et al. |
| 2012/0150286 A1 | 6/2012 | Weber et al. |
| 2012/0165868 A1 | 6/2012 | Burkhart et al. |
| 2012/0183799 A1 | 7/2012 | Steele et al. |
| 2012/0185058 A1 | 7/2012 | Albertorio et al. |
| 2012/0189833 A1 | 7/2012 | Suchanek et al. |
| 2012/0189844 A1 | 7/2012 | Jain et al. |
| 2012/0209278 A1 | 8/2012 | Ries et al. |
| 2012/0265298 A1 | 10/2012 | Schmieding et al. |
| 2013/0023907 A1 | 1/2013 | Sterrett et al. |
| 2013/0023927 A1 | 1/2013 | Cassani |
| 2013/0046312 A1 | 2/2013 | Millett et al. |
| 2013/0096563 A1 | 4/2013 | Meade et al. |
| 2013/0096612 A1 | 4/2013 | Zajac et al. |
| 2013/0103104 A1 | 4/2013 | Krupp et al. |
| 2013/0110165 A1 | 5/2013 | Burkhart et al. |
| 2013/0138108 A1 | 5/2013 | Dreyfuss et al. |
| 2013/0138150 A1 | 5/2013 | Baker et al. |
| 2013/0150885 A1 | 6/2013 | Dreyfuss |
| 2013/0165954 A1 | 6/2013 | Dreyfuss et al. |
| 2013/0165972 A1 | 6/2013 | Sullivan |
| 2013/0178871 A1 | 7/2013 | Koogle, Jr. et al. |

FOREIGN PATENT DOCUMENTS

| | | |
|---|---|---|
| AU | 2002248198 B2 | 5/2007 |
| AU | 2005202099 B2 | 6/2007 |
| AU | 2002357284 B2 | 8/2007 |
| AU | 2006202337 B2 | 5/2008 |
| AU | 2003262428 | 8/2009 |
| AU | 2007216648 B2 | 11/2009 |
| AU | 2004216106 B2 | 6/2010 |
| AU | 2008207536 B2 | 3/2011 |
| CA | 2470194 C | 2/2011 |
| DE | 2933174 | 4/1980 |
| DE | 3516743 | 11/1986 |
| DE | 3840466 | 6/1990 |
| DE | 19505083 | 11/1995 |
| EP | 0241240 | 10/1987 |
| EP | 0350780 | 1/1990 |
| EP | 0485678 | 5/1992 |

(56) References Cited

FOREIGN PATENT DOCUMENTS

| | | |
|---|---|---|
| EP | 0327387 | 9/1992 |
| EP | 0505634 | 9/1992 |
| EP | 0736292 | 10/1996 |
| EP | 0903125 | 3/1999 |
| EP | 0903127 | 3/1999 |
| EP | 0993812 | 4/2000 |
| EP | 0661023 | 8/2001 |
| EP | 1426013 | 9/2004 |
| EP | 1278460 | 4/2009 |
| EP | 2314257 | 2/2013 |
| FR | 2242068 | 3/1975 |
| FR | 2642301 | 3/1990 |
| FR | 2676917 | 12/1992 |
| FR | 2693650 | 1/1994 |
| FR | 2718014 | 10/1995 |
| FR | 2733904 | 11/1996 |
| FR | 2739151 | 3/1997 |
| GB | 2281577 | 3/1995 |
| GB | 2372707 | 9/2002 |
| JP | 61502029 | 9/1986 |
| JP | 63300758 | 12/1988 |
| JP | 3504932 | 10/1991 |
| JP | H03-092328 | 11/1992 |
| JP | 518511 | 3/1993 |
| JP | 06339490 | 12/1994 |
| JP | 11244315 | 9/1999 |
| JP | 2001525210 | 12/2001 |
| JP | 2002291779 | 10/2002 |
| JP | 2003534096 | 11/2003 |
| WO | 8803781 | 6/1988 |
| WO | 8909578 | 10/1989 |
| WO | 9427507 | 12/1994 |
| WO | 9624304 | 8/1996 |
| WO | 9722306 | 6/1997 |
| WO | 9920192 | 4/1999 |
| WO | 0013597 | 3/2000 |
| WO | 0105336 | 1/2001 |
| WO | 0166021 | 9/2001 |
| WO | 0166022 | 9/2001 |
| WO | 0182677 | 11/2001 |
| WO | 0191648 | 12/2001 |
| WO | 0191672 | 12/2001 |
| WO | 0217821 | 3/2002 |
| WO | 02086180 | 10/2002 |
| WO | 03047470 | 6/2003 |
| WO | 03051210 | 6/2003 |
| WO | 03051211 | 6/2003 |
| WO | 03061516 | 7/2003 |
| WO | 03065909 | 8/2003 |
| WO | 2004014261 | 2/2004 |
| WO | 2004026170 | 4/2004 |
| WO | 2004052216 | 6/2004 |
| WO | 2004075777 | 9/2004 |
| WO | 2005051231 | 6/2005 |
| WO | 2006004885 | 1/2006 |
| WO | 2006091686 | 8/2006 |

OTHER PUBLICATIONS

Cook, et al., "Meta-analysis of First Metatarsophalangeal Joint Implant Arthroplasty," Journal of Foot and Ankle Surgery, vol. 48, Issue 2, pp. 180-190 (2009).
Derner, "Complications and Salvage of Elective Central Metatarsal Osteotomies," Clin. Podiatr. Med. Surg. 26 (2009) 23-35.
Kirker-Head, et al., "Safety of, and Biological Functional Response to, a Novel Metallic Implant for the Management of Focal Full-Thickness Cartilage Defects: Preliminary Assessment in an Animal Model Out to 1 year," Journal of Orthopedic Research, May 2006 pp. 1095-1108.
Becher, et al. "Effects of a contoured articular prosthetic device on tibiofemoral peak contact pressure: a biomechanical study," Knee Surg Sports Traumatol Arthrosc. Jan. 2008; 16(1): 56-63.
United States Office Action dated May 13, 2009 issued in related U.S. Appl. No. 11/359,892.
United States Office Action dated May 18, 2009 issued in related U.S. Appl. No. 11/209,170.
United States Office Action dated May 1, 2009 issued in related U.S. Appl. No. 11/461,240.
Australian Office Action dated Jan. 29, 2009 issued in related Australian Patent Application No. 2004216106.
European Search Report dated Apr. 22, 2009 issued in related European Patent Application No. 09002088.4.
U.S. Office Action dated Aug. 30, 2006 issued in related U.S. Appl. No. 10/618,887.
U.S. Office Action dated Jan. 15, 2008 issued in related U.S. Appl. No. 10/618,887.
U.S. Office Action dated May 28, 2009 issued in related U.S. Appl. No. 11/359,891.
International Search Report and Written Opinion dated Jun. 1, 2009 issued in related International Patent Application No. PCT/US2009/035889.
International Preliminary Report and Patentability dated May 7, 2009 issued in related International Patent Application No. PCT/US2007/082262.
Supplemental European Search Report dated May 28, 2009 issued in related International European Patent Application No. 01997077.1.
Supplemental European Search Report dated May 11, 2009 issued in related International European Patent Application No. 02805182.9.
Notice of Allowance dated Feb. 20, 2009 issued in related U.S. Appl. No. 10/618,887.
Notice of Reasons for Rejection issued in related Japanese Patent Application No. 2003-394702 mailed Jul. 21, 2009.
Notice of Reasons for Rejection issued in related Japanese Patent Application No. 20-541615 mailed May 26, 2009.
International Preliminary Report on Patentability issued in related International Patent Application No. PCT/US2007/025284 dated Jun. 25, 2009.
Office Action issued in related Australian Patent Application No. 2007216648 dated Jul. 28, 2009.
European Search Report dated Jul. 10, 2009 issued in related European Patent Application No. 09002088.4.
International Preliminary Report on Patentability dated Aug. 20, 2009 issued in related International Patent Application No. 2008053194.
Notice of Allowance dated Aug. 25, 2009 issued in related U.S. Appl. No. 11/379,151.
Notice of Allowance dated Aug. 27, 2009 issued in related U.S. Appl. No. 10/760,965.
U.S. Office Action dated Sep. 2, 2009 issued in relation U.S. Appl. No. 10/994,453.
U.S. Office Action dated Oct. 5, 2009 issued in relation U.S. Appl. No. 10/789,545.
U.S. Office Action dated Oct. 15, 2009 issued in relation U.S. Appl. No. 11/551,912.
U.S. Office Action dated Oct. 14, 2009 issued in relation U.S. Appl. No. 11/461,240.
Australian Notice of Allowance dated Oct. 29, 2009 issued in related Australian Patent Application No. 2007216648.
Notice of Allowance dated Oct. 9, 2009 issued in related U.S. Appl. No. 10/373,463.
Australian Office Action dated Oct. 29, 2009 issued in related Australian Patent Application No. 2007203623.
Japanese Notice of Reasons for Rejection dated Sep. 8, 2009 issued in related Japanese Patent Application No. 2003552147.
Notice of Reasons for Rejection dated Nov. 17, 2009 issued in Japanese Patent Application No. 2007-519417.
European Search Report dated Dec. 3, 2009 issued in related European Patent Application No. 06735827.5.
Office Action dated Dec. 24, 2009 issued in related U.S. Appl. No. 10/994,453.
Supplemental Notice of Allowance dated Nov. 25, 2009 issued in related U.S. Appl. No. 10/373,463.
European Office Action dated Jan. 11, 2010 issued in related European Patent Application No. 2005218302.
U.S. Office Action dated Jan. 25, 2010 issued in related U.S. Appl. No. 11/326,133.

(56) References Cited

OTHER PUBLICATIONS

Australian Office Action dated Apr. 9, 2010 issued in related Australian Patent Application No. 2005260590.
U.S. Office Action dated Mar. 2, 2010 issued in related U.S. Appl. No. 11/169,326.
U.S. Office Action dated Mar. 9, 2010 issued in related U.S. Appl. No. 11/359,892.
Australian Office Action dated Feb. 26, 2010 issued in related Australian Patent Application No. 2008207536.
Supplemental Notice of Allowance dated Feb. 2, 2010 issued in related U.S. Appl. No. 10/373,463.
European office communication dated Feb. 10, 2010 issued in European Patent Application No. 09002088.4-2310.
International Search Report and Written Opinion dated Apr. 21, 2010 issued in related International Patent Application No. PCT/US2010/025095.
International Search Report and Written Opinion dated May 3, 2010 issued in related International Patent Application No. PCT/US2010/025464.
European Office Action dated Apr. 13, 2010 issued in related European Patent Application No. 02805182.9-2310.
European Office Action dated Mar. 25, 2010 issued in related European Patent Application No. 01997077.1-2310.
U.S. Office Action dated May 18, 2010 issued in related U.S. Appl. No. 12/415,503.
Japanese Notice of Reasons for Rejection dated Jun. 1, 2010 issued in related Japanese Patent Application No. 2003394702.
European Office Action dated Jun. 1, 2010 issued in related European Patent Application No. 04811836.8-2310.
Japanese Notice of Reasons for Rejection dated Jun. 29, 2010 issued in related Japanese Patent Application No. 2007519417.
Australian Office Action dated Jun. 11, 2010 issued in related Australian Patent Application No. 2005277078.
International Search Report dated Jun. 9, 2010 issued in related International Patent Application No. PCT/US2010/031594.
European Office Action dated May 7, 2010 issued in related European Patent Application No. 06733631.3-2310.
International Search Report dated Jun. 18, 2010 issued in related International Patent Application No. PCT/US2010/031602.
U.S. Office Action dated Jun. 8, 2010 issued in related U.S. Appl. No. 11/209,170.
Office Action dated Sep. 2, 2010 issued in related U.S. Appl. No. 12/415,503.
Office Action dated Aug. 30, 2010 issued in related U.S. Appl. No. 12/397,095.
Office Action dated Jul. 21, 2010 issued in related U.S. Appl. No. 11/551,912.
Office Action dated Aug. 5, 2010 issued in related U.S. Appl. No. 11/325,133.
Notice of Allowance dated Aug. 6, 2010 issued in related U.S. Appl. No. 11/359,892.
Canadian Office Action dated Jul. 29, 2010 issued in related Canadian Patent Application No. 2470936.
Supplemental European Search Report dated Aug. 9, 2010 issued in related European Patent Application No. 04714211.2-2300.
Australian Office Action dated Aug. 23, 2010 issued in related Australian Patent Application No. 2006203909.
Notice of Allowance dated Sep. 9, 2010 issued in related U.S. Appl. No. 10/994,453.
Office Action dated Sep. 21, 2010 issued in related U.S. Appl. No. 11/169,326.
Office Action dated Sep. 29, 2010 issued in related U.S. Appl. No. 11/461,240.
Office Action dated Oct. 11, 2010 issued in related Australian Patent Application No. 2006216725.
International Preliminary Report on Patentability dated Sep. 16, 2010 issued in related International Patent Application No. PCT/US2009/035889.
Supplemental Notice of Allowance dated Oct. 13, 2010 issued in related U.S. Appl. No. 10/994,453.
Supplemental Notice of Allowance dated Oct. 6, 2010 issued in related U.S. Appl. No. 12/415,503.
U.S. Office Action dated Oct. 15, 2010 received in related U.S. Appl. No. 12/027,121.
U.S. Supplemental Notice of Allowance dated Oct. 28, 2010 issued in related U.S. Appl. No. 12/415,503.
European Search Report dated Nov. 4, 2010 issued in related European Patent Application No. 07862736.1-1269.
Notice of Allowance dated Nov. 26, 2010 issued in related U.S. Appl. No. 11/209,170.
Supplemental Notice of Allowance dated Dec. 8, 2010 issued in related U.S. Appl. No. 11/209,170.
Notice of Allowance dated Dec. 13, 2010 issued in related U.S. Appl. No. 12/397,095.
Notice of Allowance dated Jan. 5, 2011 issued in related U.S. Appl. No. 11/326,133.
Supplemental Notice of Allowance dated Feb. 14, 2011 issued in related U.S. Appl. No. 11/326,133.
Canadian Office Action dated Jan. 7, 2011 issued in related Canadian Patent Application No. 2407440.
European Office Action dated Dec. 23, 2010 issued in related European Patent Application No. 028051882.9-2310.
European Office Action dated Dec. 30, 2010 issued in related European Patent Application No. 01997077.1-2310.
Extended Search Report dated Feb. 22, 2011 issued in European Patent Application No. 10012693.7, 8 pages.
Notice of Allowance dated Mar. 2, 2011 issued in Australian Patent Application No. 2008207536, 3 pages.
Notice of Allowance dated Mar. 15, 2011 issued in U.S. Appl. No. 11/551,912, 7pages.
U.S. Office Action dated Apr. 11, 2011 issued in U.S. Appl. No. 11/779,044, 10 pages.
Notice of Allowance dated Apr. 28, 2011 issued in U.S. Appl. No. 12/027,121, 9 pages.
USPTO Office action dated Dec. 8, 2005 issued in corresponding U.S. Appl. No. 10/373,463.
USPTO Office Action dated Aug. 31, 2005 issued in corresponding U.S. Appl. No. 10/308,718.
USPTO Office action dated Aug. 16, 2005 issued in corresponding U.S. Appl. No. 10/373,463.
USPTO Office action dated Jan. 27, 2005 issued in corresponding U.S. Appl. No. 10/373,463.
USPTO Office action dated Aug. 13, 2004 issued in corresponding U.S. Appl. No. 10/373,463.
USPTO Notice of Allowance issued Sep. 26, 2003 in U.S. Appl. No. 10/162,533.
USPTO Notice of Allowance issued May 12, 2003 in U.S. Appl. No. 10/024,077.
USPTO Office Action dated Apr. 1, 2003 issued in U.S. Appl. No. 10/162,533.
USPTO Office action dated Mar. 28, 2003 issued in corresponding U.S. Appl. No. 10/024,077.
USPTO Notice of Allowance issued Sep. 30, 2002 in U.S. Appl. No. 09/846,657.
USPTO Office Action dated Apr. 2, 2002 issued in corresponding U.S. Appl. No. 09/846,657.
USPTO Office Action dated Feb. 27, 2002 issued in corresponding U.S. Appl. No. 09/846,657.
USPTO Office Action dated Jan. 3, 2002 issued in corresponding U.S. Appl. No. 09/846,657.
AU Examiners report dated Jan. 18, 2006 issued in corresponding Australian patnet application No. 2005202099.
AU Examiners report dated Jan. 12, 2007 issued in corresponding Australian patnet application No. 2006202337.
AU Examiners report dated Feb. 21, 2007 issued in corresponding Australian patnet application No. 2005202099.
AU Examiners report dated May 23, 2007 issued in corresponding Australian patnet application No. 2005202099.
AU Notice of Acceptance dated Aug. 6, 2007 in Patent Application No. 20022357284.
EPO supplementary partial search report dated May 10, 2004 issued in corresponding European application 01932833.5-231-/US0114061.

(56) References Cited

OTHER PUBLICATIONS

EPO supplementary search report dated Aug. 30, 2004 issued in corresponding European application 01932833.5.
EPO Office Action dated Aug. 23, 2004, received in related EPO application No. 03 026 286.9 (4 pgs).
EPO Office Action dated Mar. 15, 2005, received in related EPO application No. 03 026 286.9, (3 pgs).
EPO Search Report received in related EPO Application No. 03 02 6286.9 dated Feb. 26, 2004 (5pgs).
EPO Search Report received in related EPO Application No. 03 02 6286.9 dated Apr. 27, 2004 (6pgs).
Examination Report dated Feb. 22, 2005 received in corresponding European Application No. 01932833.5 (3pages).
EPO Office Action dated Sep. 22, 2005 issued in corresponding European application 01932833.5-2310.
EPO Office Action dated Sep. 11, 2006 issued in corresponding European application 01932833.5-2310.
International Preliminary Examination Report dated Nov. 5, 2002 issued in corresponding PCT patent application No. PCT/US01/14061.
US Office Action issued in related U.S. Appl. No. 10/994,453 dated Feb. 25, 2008.
International Preliminary Examination Report dated Nov. 12, 2002 issued in corresponding PCT patent application No. PCT/US01/48821.
International Preliminary Examination Report dated Sep. 12, 2003 issued in corresponding PCT patent application No. PCT/US02/40310.
International Preliminary Examination Report dated Oct. 27, 2003 issued in corresponding PCT patent application No. PCT/US01/48821.
International Preliminary Examination Report dated Aug. 19, 2004 issued in corresponding PCT patent application No. PCT/US02/40310.
Notice of Allowance issued in corresponding U.S. Appl. No. 10/618,887 dated Sep. 13, 2007.
International Preliminary Report on Patentability and Written Opinion dated May 22, 2006 in corresponding PCT patent application No. PCT/US04/039181.
English language translation of Japanese Office Action dated Aug. 9, 2007 issued in corresponding Japanese application No. 2003-552148.
Canadian Office Action dated Jan. 2, 2008 issued in corresponding Canadian Application No. 2407440.
International Preliminary Report on Patentability and Written Opinion dated Mar. 1, 2007 in corresponding PCT patent application No. PCT/US05/030120.
International Preliminary Report on Patentability and Written Opinion dated Jun. 28, 2007 in corresponding PCT patent application No. PCT/US2005/005980.
International Preliminary Report on Patentability and Written Opinion dated Jul. 19, 2007 in corresponding PCT patent application No. PCT/US2006/000380.
International Search Report dated Dec. 27, 2001 issued in corresponding PCT patent application No. PCT/US01/14061.
Office Action issued in corresponding U.S. Appl. No. 10/741,044 dated Oct. 26, 2005.
International Search Report dated May 23, 2003 issued in corresponding PCT patent application No. PCT/US02/40310.
International Search Report and Written Opinion dated Dec. 30, 2004 issued in corresponding PCT patent application No. PCT/US04/05539.
International Search Report and Written Opinion dated Jan. 30, 2006 issued in corresponding PCT patent application No. PCT/US04/39181.
International Search Report and Written Opinion dated Aug. 30, 2006 issued in corresponding PCT patent application No. PCT/US06/06323.
International Search Report and Written Opinion dated Sep. 29, 2006 issued in corresponding PCT patent application No. PCT/US05/30120.
International Search Report and Written Opinion dated Nov. 27, 2006 issued in corresponding PCT patent application No. PCT/US06/00380.
International Search Report and Written Opinion dated Nov. 29, 2006 issued in corresponding PCT patent application No. PCT/US05/023200.
International Search Report and Written Opinion dated May 22, 2007 issued in corresponding PCT patent application No. PCT/US05/05980.
International Preliminary Report on Patentability dated Sep. 1, 2011 issued in PCT International Patent Application No. PCT/US2010/025095, 8 pages.
International Preliminary Report on Patentability dated Oct. 27, 2011 issued in PCT International Patent Application No. PCT/US2010/031602, 8 pages.
International Preliminary Report on Patentability dated Oct. 27, 2011 issued in PCT International Patent Application No. PCT/US2010/031594, 7 pages.
U.S. Office Action dated Nov. 1, 2011 issued in U.S. Appl. No. 12/713,135, 10 pages.
U.S. Notice of Allowance dated Nov. 23, 2011 issued in U.S. Appl. No. 11/623,513, 19 pages.
U.S. Office Action dated Nov. 28, 2011 issued in U.S. Appl. No. 12/711,039, 6 pages.
Examination Report dated Dec. 30, 2011 issued in European Patent Application No. 09 002 088.4, 6 pages.
Intent to Grant dated Feb. 17, 2012 issued in European Patent Application No. 02 805 182.9, 5 pages.
Notice of Allowance dated Feb. 24, 2012 issued in U.S. Appl. No. 12/027,121, 9 pages.
Intent to Grant dated Feb. 29, 2012 issued in European Patent Application No. 10 012 693.7, 5 pages.
Supplemental Notice of Allowance dated Mar. 2, 2012 issued in U.S. Appl. No. 12/027,121, 2 pages.
Office Action dated Mar. 2, 2012 issued in U.S. Appl. No. 12/713,135, 7 pages.
Habermeyer, Peter, ATOS News, Oct. 2005, "The Artificial Limb "Eclipse"—A new draft without shank in the implantation of artificial shoulder limbs", cover page w/pp. 40-41, with English translation dated Jan. 13, 2006 (2 pgs).
Thermann, et al, ATOS Newsletter, Jun. 2005, Aktuelle Therrien, (16 pages).
Gray, Henry, Anatomy of the Human Body, 1918, 6d. The Foot 1. The Tarsus, II. Osteology, cover page and 10 pgs, www.Bartleby.com/107/63.html#i268 Oct. 25, 2004.
Chainsaw, Wikipedia, the free encyclopedia, http://en.wikipedia.org/w/index.php?title=Chainsaw&printable=yes, Jun. 26, 2007 (3 pages).
APTA | Knee,/http://www.apta.org/AM/PrinerTemplate.cfm?Section=Home&TEMPLATE=/CM/HTMLDisplay.dfg& . . . Jun. 25, 2007 (1page).
American Machinist, Full-radius milling cutters, http://www.americanmachinist.com/Classes/Article/ArticleDraw_P.aspx, Jun. 26, 2007 (1 page).
Chuck (engineering),Wikipedia, the free encyclopedia, http://en.wikipedia.org/w/index.php?title=Chuck_%28engineering%29&printable=yes, Jun. 25, 2007, (4 pages).
Dovetail Rails, http://www.siskiyou.com/MDRSeries.htm, Jun. 25, 2007 (2 pages).
Knee Resurfacing, Permedica, GKS, Global Knee System. Cod. 104570 vers 1.0 del Mar. 15, 2006 (8pages).
Makita Industrial Power Tools, Product Details Print Out, Chain Mortiser, http://www.makita.com/menu.php?pg=product_det_prn&tag=7104L, Jun. 26, 2007 (3pgs).
Milling machine, Wikipedia, the free encyclopedia, http://en.wikipedia.org/w/index.php?title=Milling_machine&printable=yes, Jun. 26, 2007 (4 pages).
Mortise and tenon, Wikipedia, the free encyclopedia, http://en.wikipedia.org/w/index.php?title=Mortise_and_tenon&printable=yes, Jun. 25, 2007 (3 pages).

(56) References Cited

OTHER PUBLICATIONS

Oka et al, "Development of artificial articular cartilage", Proc Instn Mech Engrs vol. 214 Part H, 2000 pp. 59-68 (10 pages).
M. Siguier, MD et al, "Preliminary Results of Partial Surface Replacement of the Femoral Head in Osteonecrosis", The Jorunal of Arthroplasty, vol. 14, No. 1, 1999, pp. 45-51.
T. Siguier, MD et al, Partial Resurfacing Arthroplasty of the Femoral Head in Avascular Necrosis, Clinical Orthopaedics and Related Research, No. 386, 2001, pp. 85-92.
Suganuma, et al—"Arthroscopically Assisted Treatment of Tibial Plateau Fractures", Arthroscopy: The Journal of Arthroscopic and Related Surgery, vol. 20, No. 10, Dec. 2004, pp. 1084-1089 (6 pages).
The Mini Uni: A New Solution for Arthritic Knee Pain and Disability, AORI, 4 pages, www.aori.org/uniknee.htm Apr. 20, 2004.
The Stone Clinic, Orthopaedic Surgery Sports Medicine and Rehabilitation, Unicompartmental Replacement (partial knee joint replacement), Aug. 21, 2000, 3 pages, www.stoneclinic.com/unicopartrepl.htm, Apr. 20, 2004.
Ushio et al, "Partial hemiarthroplasty for the treatment of osteonecrosis of the femoral head", An Experimantal Study in the Dog, The Journal of Bone and Joint Surgery, vol. 85-B, No. 6, Aug. 2003, pp. 922-930 (9 pages).
Russell E. Windsor, MD, In-Depth Topic Reviews, Unicompartmental Knee Replacement, Nov. 7, 2002, 9 pages.
Yaw angle, Wikipedia, the free encyclopedia, http://en.wikipedia.org/w/index.php?title=Yaw_angle&printable=yes, Jun. 25, 2007 (1 page).
Bale, MD, Reto J., et al, "Osteochondral Lesions of the Talus: Computer=assisted Retrograde Drilling Feasibility and Accuracy in Initial Experriences", (Radiology. 2001;218:278-282) © RSNA, 2001.
Biomet/Copeland, "Aequalis® Resurfacing Head" Tornier, Scientific Vision, Surgical Leadership, SS-401 Jan. 2007.
Kumai, M.D., Tsukasa, et al Arthroscopic Drilling for the Treatment of Osteochondral Lesions of the Talus*, The Journal of Bone & Joint Surgery, American vol. 81:1229-35(1999).
Matsusue, M.D., Yoshitaka, et al, "Arthroscopic Osteochondral Autograft Transplantation for Chondral Lesion of the Tibial Plateau of the Knee", Arthroscopy: The Journal of Arthroscopic and Related Surgery, vol. 17, No. 6 (Jul.-Aug.), 2001:pp. 653-659.
Pill M.S., P.T., Stephan G. et al, "Osteochondritis Dissecans of the Knee: Experiences at the Children's Hospital of Philadelphia and a Review of Literature", The University of Pennsylvania Orthopaedic Journal 14: 25-33, 2001.
Schneider, T., et al, "Arthroscopy of the ankle joint. A list of indications and realistic expectations", Foot and Ankle Surgery 1996 2:189-193, © 1996 Arnette Blackwell SA.
Taranow WS, et al, "Retrograde drilling of osteochondral lesions of the medial talar dome", PubMed, www.pubmed.gov, A service of the National Library of Medicing and the Natinal Institutes of Health, Foot Ankle Int. Aug. 1999; 20(8):474-80.
Ueblacker, M.D., Peter, et al, "Retrograde Cartilage Transplantation of the Proximal and Distal Tibia", Arthroscopy: The Journal of Arthroscipic and Related Surgery, vol. 20, No. 1 Jan. 2004: pp. 73-78.
USPTO Office Action dated Dec. 21, 2007 issued in corresponding U.S. Appl. No. 11/169,326.
USPTO Office Action dated Dec. 26, 2007 issued in U.S. Appl. No. 11/379,151.
USPTO Office Action dated Oct. 9, 2007 issued in U.S. Appl. No. 10/373,463.
USPTO Office Action dated Aug. 29, 2007 issued in U.S. Appl. No. 10/760,965.
USPTO Office Action dated May 31, 2007 issued in corresponding U.S. Appl. No. 11/326,133.
USPTO Office Action dated Apr. 26, 2007 issued in U.S. Appl. No. 10/373,463.
USPTO Office Action dated Apr. 4, 2007 issued in corresponding U.S. Appl. No. 10/789,545.
USPTO Office Action dated Mar. 15, 2007 issued in U.S. Appl. No. 10/760,965.
USPTO Office Action dated Feb. 20, 2007 issued in corresponding U.S. Appl. No. 11/326,133.
USPTO Office Action dated Nov. 6, 2006 issued in U.S. Appl. No. 10/760,965.
USPTO Office Action dated Oct. 17, 2006 issued in U.S. Appl. No. 10/373,463.
USPTO Office Action dated Oct. 31, 2006 issued in U.S. Appl. No. 10/760,965.
USPTO Office Action dated Jul. 25, 2006 issued in U.S. Appl. No. 10/760,965.
USPTO Office action dated May 10, 2006 issued in corresponding U.S. Appl. No. 10/373,463.
USPTO Office Action dated Apr. 21, 2006 issued in corresponding U.S. Appl. No. 10/308,718.
USPTO Office Action dated Nov. 9, 2005 issued in corresponding U.S. Appl. No. 10/308,718.
International Search Report and Written Opinion dated Aug. 8, 2007 issued in corresponding PCT patent application No. PCT/US06/29875.
Notice of Allowance issued in corresponding U.S. Appl. No. 10/308,718 dated Sep. 11, 2006.
Office Action issued in corresponding U.S. Appl. No. 11/326,133 dated Oct. 17, 2007.
United States Office Action issued is related U.S. Appl. No. 10/760,965 dated Feb. 19, 2008.
Australian Office Action issued in related Australian Patent Application No. 2003262428 dated Mar. 20, 2008.
Australian Office Action issued in related Australian Patent Application No. 2004293042 dated Feb. 20, 2008.
U.S. Office Action issued in related U.S. Appl. No. 11/326,133 dated Jun. 12, 2008.
International Search Report and Written Opinion dated Jun. 24, 2008 issued in related International Patent Application No. PCT/US07/73685.
International Search Report and Written Opinion dated Jun. 11, 2008 issued in related International Patent Application No. PCT/US07/25284.
International Search Report and Written Opinion dated Aug. 8, 2008 issued in related International Patent Application No. PCT/US08/53988.
U.S. Office Action issued in related U.S. Appl. No. 10/994,453 dated Jun. 5, 2007.
Japanese Office Action dated Jul. 22, 2008 issued in related Japanese Patent Application No. 2006-501193.
U.S. Office Action issued in related U.S. Appl. No. 10/373,463 dated Apr. 21, 2008.
Notice of Allowance received in U.S. Appl. No. 10/618,887 dated Aug. 15, 2008.
Australia Office Action issued in related Australian Patent Application No. 2007216648 dated May 30, 2008.
European Office Action issued in related European Patent Application No. 01932833.5-2310 dated Apr. 25, 2008.
U.S. Office Action received in related U.S. Appl. No. 11/169,326 dated Jun. 30, 2008.
U.S. Office Action received in related U.S. Appl. No. 11/169,326 dated Jul. 27, 2007.
U.S. Office Action received in related U.S. Appl. No. 11/169,326 dated Apr. 17, 2007.
U.S. Office Action received in related U.S. Appl. No. 11/169,326 dated Mar. 9, 2007.
Canadian Office Action issued in related Canadian Patent Application No. 2546582 dated Aug. 21, 2008.
U.S. Office Action issued in related U.S. Appl. No. 10/994,453 dated Sep. 3, 2008.
U.S. Office Action dated Oct. 21, 2008 issued in related U.S. Appl. No. 11/461,240.
U.S. Office Action dated Jun. 25, 2008 issued in related U.S. Appl. No. 11/359,891.
U.S. Office Action dated Sep. 25, 2008 issued in related U.S. Appl. No. 11/326,133.
U.S. Office Action dated Jul. 2, 2008 issued in related U.S. Appl. No. 11/379,151.

(56) References Cited

OTHER PUBLICATIONS

European Office Action dated Oct. 6, 2008 issued in related European Patent Application No. 01932833.5-2310.
U.S. Office Action dated Jun. 27, 2008 issued in related U.S. Appl. No. 10/760,965.
International Search Report and Written Opinion dated Oct. 1, 2008 issued in related International Patent Application No. PCT/US08/53194.
International Search Report and Written Opinion dated Oct. 9, 2008 issued in related International Patent Application No. PCT/US07/82262.
European Search Report dated Nov. 4, 2008 issued in related European Patent Application No. 04811836.8-2310.
U.S. Office Action dated Jan. 9, 2009 issued in related U.S. Appl. No. 10/373,463.
Canadian Office Action dated Dec. 9, 2008 issued in related Canadian Patent Application No. 2407440.
Supplemental European Search Report dated Nov. 6, 2008 issued in related European Patent Application No. 05791453.3-2310.
Japanese Office Action dated Dec. 19, 2008 issued in Japanese Patent Application No. 2006501193.
Japanese Office Action dated Jan. 13, 2009 issued in Japanese Patent Application No. 2003552147.
International Search Report dated Jan. 30, 2006 issued in related International Patent Application No. PCT/US04/39181.
U.S. Office Action dated Mar. 27, 2009 issued in related U.S. Appl. No. 11/169,326.
European Office Action dated Feb. 26, 2009 in related European Patent Application No. 05791453.3.
McCarty, III., et al., "Nonarthoplasty Treatment of Glenohumeral Cartilage Lesions," Arthroscopy, The Journal of Arthroscopic and related Surgery, vol. 21, No. 9; Sep. 2005 (pp. 1131-1142).
Bushnell, et al., "Bony Instability of the Shoulder," Arthroscopy, The Journal of Arthroscopic and related Surgery, vol. 24, No. 9; Sep. 2005 (pp. 1061-1073).
Scalise, et al., "Resurfacing Arthroplasty of the Humerus: Indications, Surgical Technique, and Clinical Results," Techniques in Shoulder and Elbow Surgery 8(3):152-160; 2007.
Davidson, et al., "Focal Anatomic Patellofemoral Inlay Resurfacing: Theoretic Basis, Surgical Technique, and Case Reports," Orthop. Clin. N. Am., 39 (2008) pp. 337-346.
Provencher, et al., "Patellofemoral Kinematics After Limited Resurfacing of the Trochlea," The Journal of Knee Surgery, vol. 22 No. 2 (2008) pp. 1-7.
Dawson, et al., "The Management of Localized Articular Cartilage Lesions of the Humeral Head in the Athlete," Operative Techniques in Sports Medicine, vol. 16, Issue 1, pp. 14-20 (2008).
Uribe, et al., "Partial Humeral Head Resurfacing for Osteonecrosis," Journal of Shoulder and Elbow Surgery, (2009) 6 pages.
Burks, "Implant Arthroplasty of the First Metatarsalphalangeal Joint," Clin. Podiatr. Med. Surg., 23 (2006) pp. 725-731.
Hasselman, et al., "Resurfacing of the First Metatarsal Head in the Treatment of Hallux Rigidus," Techniques in Foot & Ankle Surgery 7(1):31-40, 2008.
Jäger, et al., "Partial hemi-resurfacing of the hip joint—a new approach to treat local osteochondral defects?" Biomed Tech 2006; 51:371-376 (2006).
Notice of Allowance dated Dec. 12, 2011 issued in U.S. Appl. No. 12/582,345, 19 pages.
U.S. Office Action dated Dec. 22, 2011 issued in U.S. Appl. No. 11/623,513, 8 pages.
U.S. Office Action dated Dec. 27, 2011 issued in U.S. Appl. No. 12/620,309, 10 pages.
U.S. Office Action dated Jan. 4, 2012 issued in U.S. Appl. No. 12/001,473, 19 pages.
U.S. Office Action dated Jan. 10, 2012 issued in U.S. Appl. No. 12/031,534, 9 pages.
U.S. Office Action dated Jan. 18, 2012 issued in U.S. Appl. No. 12/778,055, 9 pages.
European Office Action dated Jan. 23, 2012 issued in European Patent Application No. 01 997 077.1, 3 pages.
Ascension Orthopedics, Inc., Ascension Orthopedics Announces Market Release of TITAN™ Inset Mini Glenoid, PR Newswire, downloaded from internet Jul. 18, 2011, http://www.orthospinenews.com/ascension-orthopedics-announces-market-release-of-titan™-inset-mini-glenoid, Jul. 6, 2011, 2 pages.
PCT International Preliminary Report on Patentability dated Sep. 9, 2011 issued in PCT Patent Application No. PCT/US2010/025464, 7 pages.
U.S. Office Action dated Mar. 29, 2012 issued in U.S. Appl. No. 10/789,545, 7 pages.
U.S. Office Action dated Apr. 18, 2012 issued in U.S. Appl. No. 12/725,181, 9 pages.
U.S. Notice of Allowance dated May 31, 2012 issued in U.S. Appl. No. 11/623,513, 5 pages.
Extended European Search report mailed Dec. 10, 2012 issued in European Patent Application No. 07844549.1, 6 pages.
Supplementary European Search Report dated Jan. 3, 2013 issued in European Patent Application No. 05763817.3, 3 pages.
Great Britain Examination Report dated Feb. 6, 2013 issued in Great Britain Patent Application No. 1114417.7, 2 pages.
Supplementary European Search Report dated Feb. 18, 2013 issued in European Patent Application No. 08729178.7, 10 pages.
Canadian Office Action dated Dec. 13, 2012 issued in Canadian Patent Application No. 2,407,440, 6 pages.
International Search Repoort and Written Opinion dated Mar. 8, 2013 issued in PCT Patent Application No. PCT/US12/71199, 13 pages.
U.S. Office Action dated Apr. 15, 2013 issued in U.S. Appl. No. 13/470,678, 10 pages.
U.S. Office Action dated Apr. 22, 2013 issued in U.S. Appl. No. 12/001,473, 16 pages.
U.S. Office Action dated Apr. 23, 2013 issued in U.S. Appl. No. 13/037,998, 8 pages.
European Intent to Grant dated Apr. 29, 2013 issued in European Patent Application No. 07 862 736.1, 7 pages.
U.S. Notice of Allowance dated May 9, 2013 issued in U.S. Appl. No. 12/725,181, 6 pages.
U.S. Office Action dated May 15, 2013 issued in U.S. Appl. 12/762,948, 10 pages.
Preliminary Report on Patentability dated Sep. 20, 2012 issued in PCT Patent Application No. PCT/US2011/027451, 3 pages.
Notice of Allowability dated Oct. 9, 2012, issued in U.S. Appl. No. 12/713,135, 5 pages.
Notice of Allowability dated Oct. 11, 2012, issued in U.S. Appl. No. 11/169,326, 2 pages.
U.S. Office Action dated Oct. 23, 2012, issued in U.S. Appl. No. 13/042,382, 17 pages.
U.S. Office Action dated Oct. 24, 2012, issued in U.S. Appl. No. 12/942,923, 9 pages.
U.S. Office Action dated Oct. 31, 2012, issued in U.S. Appl. No. 13/075,006, 9 pages.
Notice of Allowance dated Nov. 13, 2012 issued in U.S. Appl. No. 12/725,181, 5 pages.
Final Office Action dated Aug. 13, 2012 issued in U.S. Appl. No. 12/711,039, 12 pages.
Office Action dated Aug. 14, 2012 issued in U.S. Appl. No. 12/001,473, 17 pages.
Office Action dated Aug. 20, 2012 issued in U.S. Appl. No. 13/037,998, 11 pages.
Office Action dated Aug. 21, 2012 issued in U.S. Appl. No. 13/043,430, 11 pages.
U.S. Office Action dated Aug. 28, 2012 issued in U.S. Appl. No. 12/762,948, 12 pages.
U.S. Notice of Allowance dated Sep. 4, 2012 issued in U.S. Appl. No. 11/169,326, 6 pages.
Extended Search Report dated Jul. 3, 2012 issued in European Patent Application No. 12002103.5, 5 pages.
Decision to Grant dated Jul. 26, 2012 issued in European Patent Application No. 10012693.7, 1 page.

(56) References Cited

OTHER PUBLICATIONS

U.S. Office Action dated Feb. 25, 2013 issued in U.S. Appl. No. 12/762,920, 8 pages.
U.S. Applicant Initiated Interview Summary dated May 15, 2013 issued in U.S. Appl. No. 12/762,920, 3 pages.
U.S. Final Office Action dated Jun. 24, 2013 issued in U.S. Appl. No. 13/042,382, 28 pages.
European Office Action dated Apr. 16, 2013 issued in European Patent Application No. 12 002 103.5, 5 pages.
European Office Action dated May 15, 2013 issued in European Patent Application No. 05 763 817.3, 4 pages.
U.S. Office Action dated Jul. 11, 2013 issued in U.S. Appl. No. 12/711,039, 10 pages.
U.S. Notice of Allowance dated Jul. 29, 2013 issued in U.S. Appl. No. 12/725,181, 7 pages.
U.S. Final Office Action dated Jul. 30, 2013 issued in U.S. Appl. No. 13/075,006, 10 pages.
U.S. Corrected Notice of Allowance dated Jul. 30, 2013 issued in U.S. Appl. No. 11/623,513, 2 pages.

* cited by examiner

SYSTEM AND METHOD FOR RETROGRADE PROCEDURE

CROSS-REFERENCE TO RELATED APPLICATIONS

This application is a continuation of U.S. patent application Ser. No. 11/209,170 (now U.S. Pat. No. 7,901,408), filed Aug. 22, 2005 which claims the benefit of U.S. Provisional Patent Application Ser. No. 60/603,473, filed Aug. 20, 2004. This application is a continuation of U.S. patent application Ser. No. 11/209,170 (now U.S. Pat. No. 7,901,408), filed Aug. 22, 2005 which is also a continuation-in-part of U.S. patent application Ser. No. 11/169,326, filed Jun. 28, 2005, which claims the benefit of U.S. Provisional Patent Application Ser. No. 60/583,549, filed Jun. 28, 2004. This application is a continuation of U.S. patent application Ser. No. 11/209,170 (now U.S. Pat. No. 7,901,408), filed Aug. 22, 2005 which is also a continuation in part of U.S. patent application Ser. No. 10/994,453 (now U.S. Pat. No. 7,896,885), filed Nov. 22, 2004 which claims the benefit of U.S. Provisional Patent Application Ser. No. 60/523,810, filed Nov. 20, 2003. Additionally, this application is a continuation of U.S. patent application Ser. No. 11/209,170 (now U.S. Pat. No. 7,901,408), filed Aug. 22, 2005 which is also a continuation in part of U.S. patent application Ser. No. 10/308,718 (now U.S. Pat. No. 7,163,541), filed Dec. 3, 2002. Then entire disclosures of all of the above listed applications are incorporated herein by reference.

FIELD

The present disclosure is directed at a system and method for accessing an articular joint surface. The present disclosure is further directed at a method and system for replacing at least a portion of an articular surface.

BACKGROUND

Articular cartilage, found at the ends of articulating bone in the body, is typically composed of hyaline cartilage, which has many unique properties that allow it to function effectively as a smooth and lubricious load bearing surface. Hyaline cartilage problems, particularly in knee, hip joints, and should joints, are generally caused by disease such as occurs with rheumatoid arthritis or wear and tear (osteoarthritis), or secondary to an injury, either acute (sudden), or recurrent and chronic (ongoing). Such cartilage disease or deterioration can compromise the articular surface causing pain and eventually, loss of joint movement. As a result, various methods have been developed to treat and repair damaged or destroyed articular cartilage.

For smaller defects, traditional options for this type of problem include leaving the lesions or injury alone and living with it, or performing a procedure called abrasion arthroplasty or abrasion chondralplasty. The principle behind this procedure is to attempt to stimulate natural healing. The bone surface is drilled using a high speed rotary burr or shaving device and the surgeon removes about 1 mm of bone from the surface of the lesion. This creates an exposed subchondral bone bed that will bleed and will initiate a fibrocartilage healing response. One problem with this procedure is that the exposed bone is not as smooth as it originally was following the drilling and burring which tends to leave a series of ridges and valleys, affecting the durability of the fibrocartilage response. Further, although this procedure can provide good short term results, (1-3 years), fibrocartilage is seldom able to support long-term weight bearing and is prone to wear, soften and deteriorate.

Another procedure, called Microfracture incorporates some of the principles of drilling, abrasion and chondralplasty. During the procedure, the calcified cartilage layer of the chondral defect is removed. Several pathways or "microfractures" are created to the subchondral bleeding bone bed by impacting a metal pick or surgical awl at a minimum number of locations within the lesion. By establishing bleeding in the lesion and by creating a pathway to the subchondral bone, a fibrocartilage healing response is initiated, forming a replacement surface. Results for this technique may be expected to be similar to abrasion chondralplasty.

Another means used to treat damaged articular cartilage is a cartilage transplant. Essentially, this procedure involves moving cartilage from an outside source or other knee or from within the same knee into the defect. Typically, this is done by transferring a peg of cartilage with underlying bone and fixing it in place with a screw or pin or by a press fit. Although useful for smaller defects, large defects present a problem, as this procedure requires donor pegs proportionate to the recipient bed. Large diameter lesions may exceed the capacity to borrow from within the same knee joint and rule out borrowing from another source.

Larger defects, however, generally require a more aggressive intervention. Typically treatment requires replacing a portion or all of the articular surface with an implant or prosthetic having an outer layer that that is polished or composed of a material that provides a lubricious load bearing surface in approximation of an undamaged cartilage surface. Replacement of a portion, or all, of the articular surface requires first cutting, boring, or reaming the damaged area to remove the damaged cartilage. A recess to receive an implant or prosthetic is formed at the damaged site. The implant or prosthetic is then secured to the bone in an appropriate position in the recess.

The treatment and/or replacement procedure often requires direct access to the damaged surface of the cartilage. While the most commonly damaged portions of some joints may easily be accessed for repair using a minimally invasive procedure some joints are not nearly as accessible. For example, the superior or medial femoral head, the medial humeral head, the glenoid, etc. do not permit direct access sufficient to carry out replacement of the articular surface in a minimally invasive manner. In fact, repair of such obstructed joints often requires an invasive procedure and necessitates complete dislocation of the joint. Procedures of such an invasive nature may be painful and require an extended recovery period.

Accordingly, it is an object of the present invention to provide a method for replacing an articular joint surface that is obscured from axial approach that is less invasive than conventional procedures and may not necessitate completely dislocating the joint.

BRIEF DESCRIPTION OF THE DRAWINGS

The subject matter of the present disclosure is set forth by description of embodiments consistent therewith, which description should be considered in combination with the accompanying drawings, wherein.

DESCRIPTION

By way of overview, the present disclosure provides a retrograde articular surface replacement system that may include a method and apparatus for replacing at least a portion of an articular surface including accessing a desired portion of the articular surface through a portion of bone. While the preceding overview and the following specific embodiments of the system according to the present disclosure are directed at a system for replacing at least a portion of an articular surface, the system herein may be used in connection with procedures other than the replacement of portions of an articular surface. From a broad standpoint, the system disclosed herein may provide an apparatus and method for accessing a bone, joint, etc., indirectly.

Figure 1:
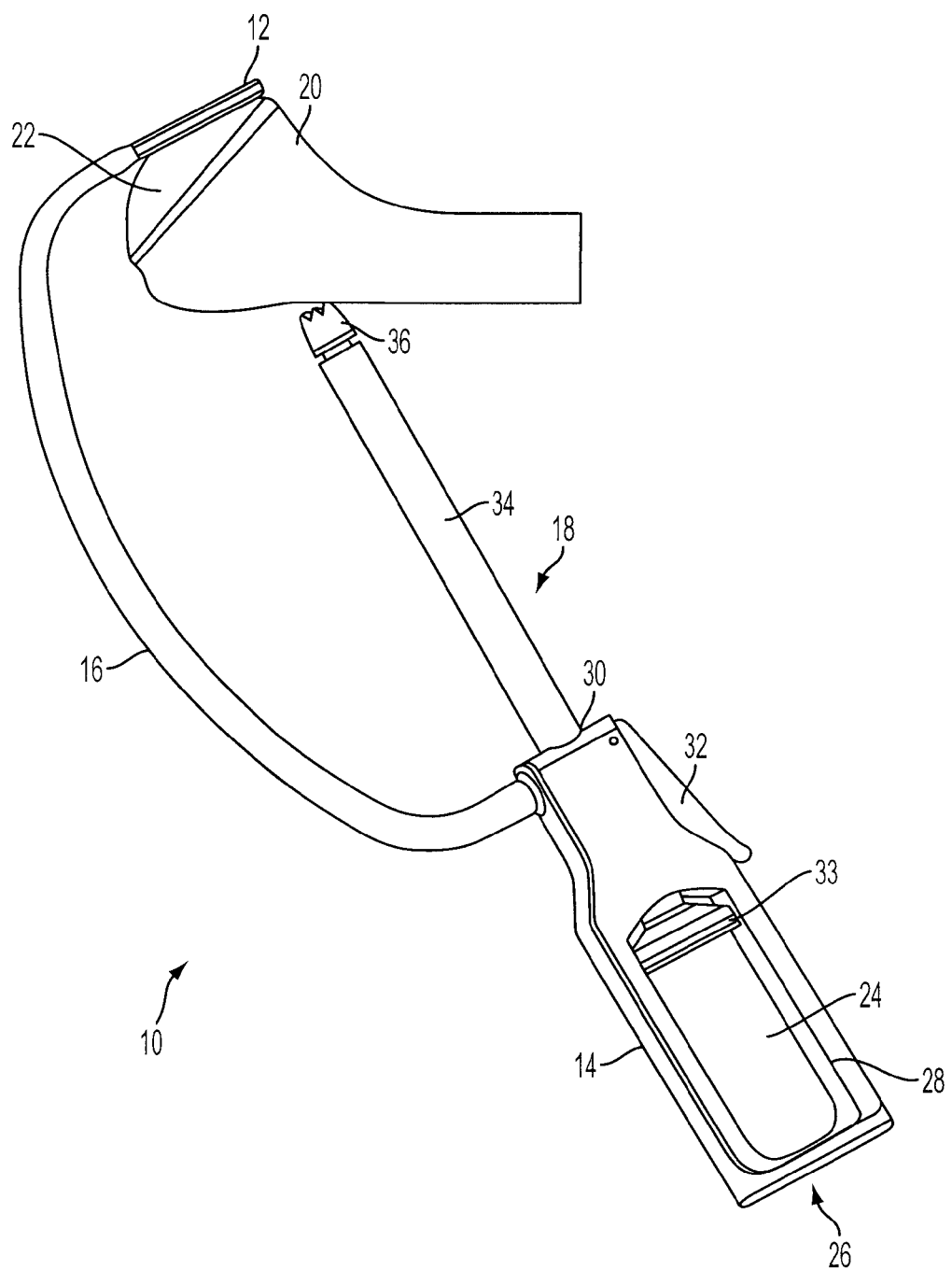
FIG. 1 illustrates an embodiment of a retrograde articular surface replacement system consistent with the present disclosure.

Turning to FIG. 1, an embodiment of a retrograde articular surface replacement system 10 is illustrated. The system 10 may generally include a locating device, such as locating hoop 12, coupled to a guide, such as a cannulated shaft 18. The locating hoop 12 and the cannulated shaft 18 may be maintained in a positional and angular relationship by an arm 16. Consistent with the illustrated embodiment, the cannulated shaft 18 may be coupled to a tool support 14, and the tool support 14 may be coupled to the locating device 12 by an arm 16. The locating hoop 12 and the cannulated shaft 18 may be positioned in an opposed arrangement around a bone 20 having an articular surface 22.

The locating hoop 12 may include an opening there through such that when the locating hoop 12 is disposed on the articular surface 22 a portion of the articular surface may be exposed through the opening of the locating hoop 12. Furthermore, when the locating hoop 12 is disposed on the articular surface 22 the locating hoop 12 may achieve a desired orientation relative to a portion of the articular surface 22 exposed through the opening of the locating hoop 12. According to the illustrated embodiment, the locating hoop 12 may generally be configured as a ring having a circular opening extending therethrough. As shown, the locating hoop 12 may be positioned on an articular surface 22. According to one embodiment, when the locating hoop 12 is positioned on the articular surface 22 the locating hoop 12 may be oriented such that the axis of the opening of the locating hoop 12 may be generally normal to the articular surface 22 at the point of intersection by the axis of the opening. According alternative embodiments, the locating hoop 12 may achieve various other desired orientations relative to the articular surface 22.

The tool support 14 may include an opening 24 extending inwardly from a rear portion 26 of the tool support 14. The tool support 14 may define one or more windows 28 to the opening 24. According to one embodiment, the window 28 may include a transparent region of the tool support 14. For example, the window 28 may include a transparent plastic, glass, etc. region allowing the interior of the opening 24 to be viewed. Alternatively, the window 28 may be provided as an opening in a side region of the tool support 14. In such a configuration, the window 28 may not only allow the interior of the opening 24 to be viewed, but may also allow the interior of the opening 24 to be accessed and/or allow tools and/or objects within the opening 24 to be manipulated from the exterior of the tool support 14.

The tool support 14 may also include a bore 30 extending from the opening 24 to a front region of the tool support 14. As shown, the bore 30 may be sized to receive the cannulated shaft 18 therethrough. According to one embodiment, the inside diameter of the bore 30 may be closely sized to the outside diameter of the cannulated shaft 18 to maintain the cannulated shaft 18 in substantially coaxial alignment with the bore 30. Additionally, the tool support 14 may include a locking mechanism 32 that may be engaged to resist axial and/or rotational movement of the cannulated shaft 18. Suitable locking mechanisms 32 may have a variety of configurations. For example, the locking mechanism 32 may be a frictional locking mechanism including a bearing member that may press against, and frictionally engage, the cannulated shaft 18. Another suitable locking mechanism 32 may include a plurality of teeth that may be selectively engaged with corresponding features, such as circumferential grooves/ridges on at least a portion of the exterior of the cannulated shaft 18. Various other locking mechanisms may also, or alternatively, be employed herein.

The locating hoop 12 and the tool support 14 may be coupled to one another by an arm 16. The arm 16 may maintain the locating hoop 12 and the tool support 14 in a desired angular alignment and or position relative to one another. For example, the arm 16 may orient the locating hoop 12 and the tool support 14 such that the axis of the bore 30 intersects the center of the opening of the locating hoop 12 at a desired angle. The arm 16 may also arrange the tool support 14 and locating hoop 12 in predetermined relative angular alignments in which the axis of the bore 30 does not intersect the opening of the locating hoop 12. According to one embodiment, the locating hoop 12 may be oriented perpendicular to the guide shaft 18.

Consistent with the illustrated embodiment, the arm 16 may be a compound arcuate member having a fixed geometry. Accordingly, the relationship between the locating hoop 12 and the tool support 14 may be fixed relationship. It is contemplated herein, however, that the arm 16 may be releasably coupled to the tool support 14 and/or the locating hoop 12. In such an embodiment the tool support 14 and/or the locating hoop 12 may be separated from the arm 16. The arm 16 may be replaced with another arm, or arm 16 and locating hoop 12 assembly, providing a different configuration and/or providing a different angular alignment and or positional relationship between the locating hoop 12 and the tool support 14. According to a related embodiment, the arm 16 may be provided as an adjustable feature, thereby allowing the angular alignment and/or positional relationship between the locating hoop 12 and the tool support 14 to be varied or modified without replacing the arm 16.

Consistent with the illustrated embodiment, the cannulated guide shaft 18 may generally include a proximal receptacle portion 33, a shaft portion 34, and a distal tip 36. The shaft portion 34 may include at least one lumen extending along the length of the cannulated shaft 18. At least a portion of the shaft 34 may be disposed in the bore 30 of the tool support 14. Desirably, the shaft 34 is sized with respect to the bore 30, to provide a minimal of clearance. Accordingly, positioning the shaft portion 34 at least partially within the bore 30 may align an axis of the lumen in a predetermined relationship relative to the axis of the bore 30. As previously discussed, the bore 30 may in turn be oriented in a predetermined angular and/or positional arrangement relative to the locating hoop 12. The locating hoop 12 may itself be arranged in a predetermined relationship to the articular surface 22. Accordingly, when the shaft 34 is at least partially disposed within the bore 30 the lumen of the shaft portion 34 may be arranged in a desired angular and/or positional orientation relative to the opening of the locating hoop 12. In one embodiment, the axis of the lumen may be oriented parallel to the axis of the bore 30 when the shaft portion 34 is at least partially received in the bore 30. In a further embodiment, the lumen may be oriented coaxial with the bore 30 when the shaft portion 34 is at least partially received in the bore 30.

Figure 4:
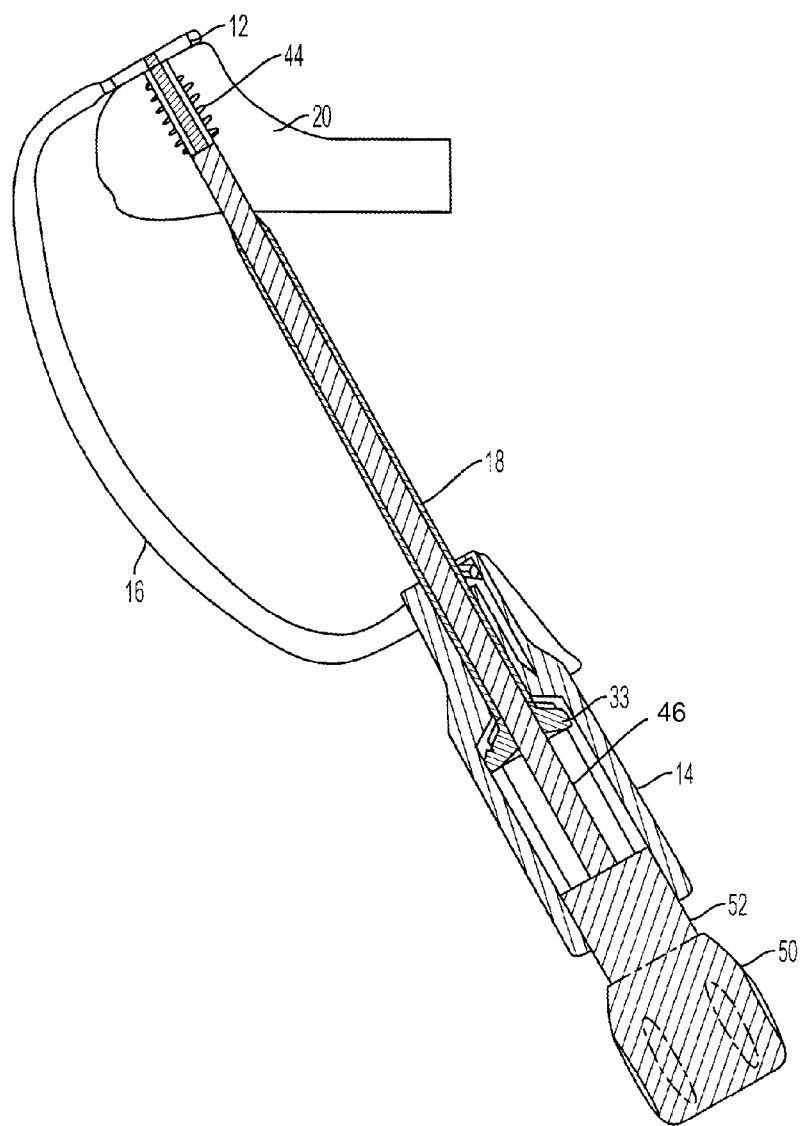
FIG. 4 is a cross-sectional view of the retrograde articular surface replacement system depicted in FIG. 3.

With additional reference to the cross-sectional view of FIG. 4, the receptacle portion 33 of the cannulated shaft 18 may include a cupped or conical interior profile leading to the lumen of the cannulated shaft 18. The cupped or conical receptacle portion 33 may facilitate the insertion of instruments, devices, etc. into the lumen of the cannulated shaft 18. Consistent with the preceding aspects, instruments, devices, etc. inserted into the lumen with the aid of the cupped or conical receptacle portion 33 may be at least generally oriented in a predetermined relationship to the opening of the locating hoop 12 by virtue of the orientation of the lumen relative to the opening of the locating hoop 12. Accordingly, instruments, devices, etc. may be at least generally placed in a predetermined orientation and/or alignment relative to a portion of the articular surface 22 identified within the locating hoop 12.

As shown in the FIG. 1, the locating hoop 12 may be positioned around a desired portion of the articular surface 22. The cannulated shaft 18 may then be inserted extending through the bore 30 of the tool support 14. The cannulated shaft 18 may be positioned so that the distal tip 36 of the cannulated shaft 18 may bear against the bone 20 opposite the articular surface 22 in the predetermined alignment relative to the opening of the locating hoop 12. As in the illustrated arrangement, when the locating hoop 12 and the distal tip 36 of the cannulated shaft 18 are positioned to bear on opposing sides of the bone 20, the distal tip 36 of the cannulated shaft 18 may contact the bone 20 at an angle. In such an orientation, only a portion of the distal tip 36 may actually contact the bone 20. The partial contact between the distal tip 36 and the bone 20 may make the distal tip 36 susceptible to moving across the surface of the bone 20, and therein altering the position of the locating hoop 12 on the articular surface 22.

Movement of the distal tip 36 of the cannulated shaft 18 across the surface of the bone 20 may be reduced by providing the distal tip 36 having biting features. For example, as shown the tip 36 may have a serrated or saw tooth end feature. When the distal tip 36 is pressed against the bone 20, the serrated end feature may engage the bone 20 and resist movement once the tip 36 is so engaged. Accordingly, the system 10 may be placed in a desired position and/or alignment relative to the articular surface 22 by positioning the bone between the locating hoop 12 and the distal tip 36 of the cannulated shaft 18. The locating hoop 12 and distal tip 36 may be brought to bear on opposing sides of the bone 20. The cannulated shaft 18 may then be locked in position using the locking mechanism 32 of the tool support 14. Accordingly, it may be possible to maintain the system 10 in the desired position and/or alignment relative to the articular surface even when the desired position causes the distal tip 36 of the cannulated shaft 18 to contact the bone at an angle such that only a portion of the distal tip 36 contacts the bone 20.

Figure 2:
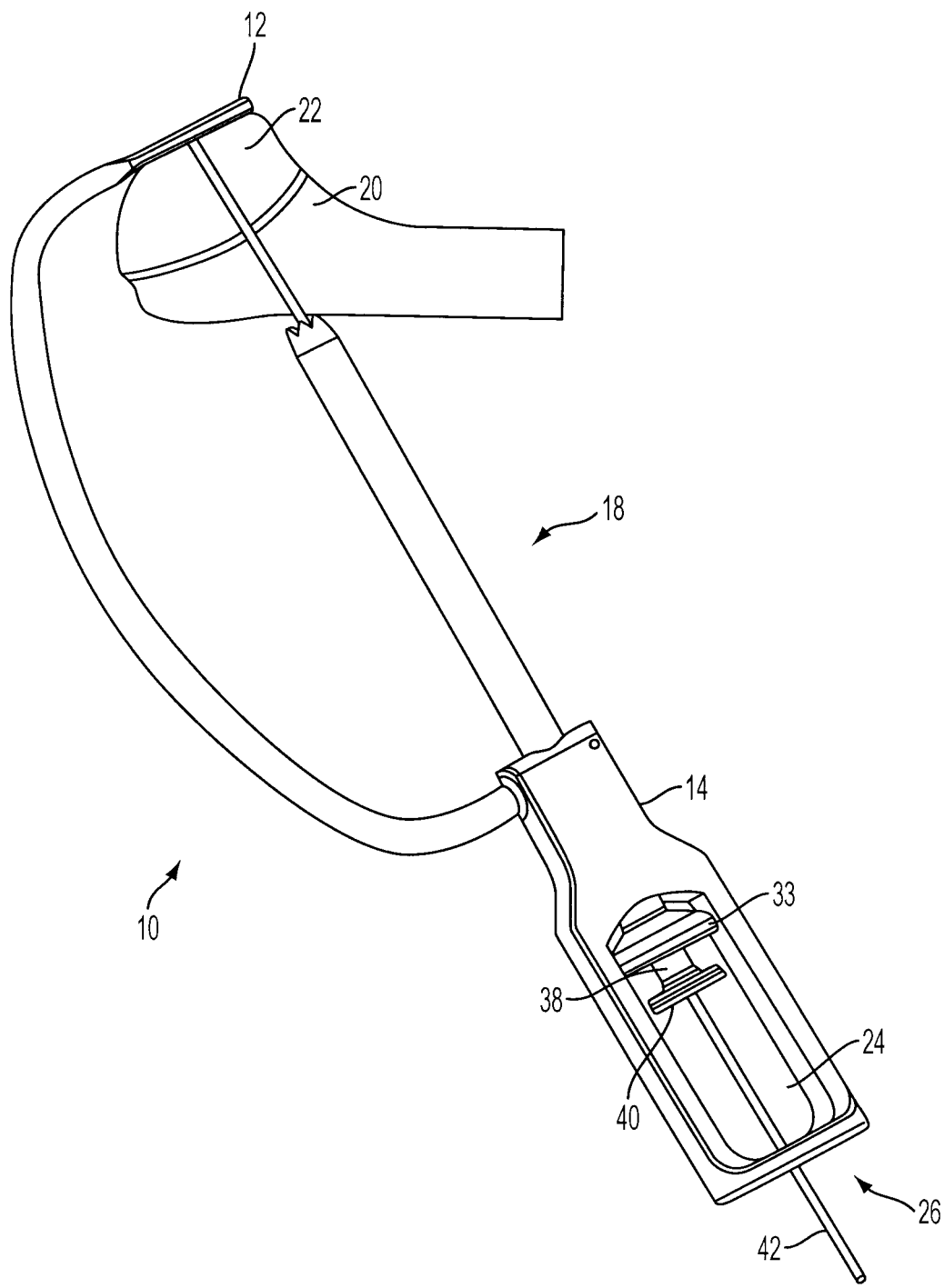
FIG. 2 illustrates the use of the retrograde articular surface replacement system of FIG. 1 to position a guide pin in a bone.

Turning to FIG. 2, a system 10 consistent with FIG. 1 may be used in a procedure for replacing a portion of an articular surface 22. According to an embodiment of the procedure consistent with the present disclosure, once the locating hoop 12 and the cannulated shaft 18 are oriented in a desired alignment relative to the articular surface 22, a reference axis may be established relative to the articular surface 22. According to one embodiment, establishing the reference axis may include providing a passage or hole through the bone 20. The passage or hole may pass all the way through the bone 20 and exit the articular surface 22. This may allow the alignment and orientation of the reference axis relative to the articular surface 22 to be verified.

A reference axis may be established, consistent with the present disclosure, by drilling a hole through the bone 20 in a predetermined alignment relative to the cannulated shaft 18. According to one embodiment, the hole may be aligned coaxially with the cannulated shaft 18. Consistent with the present disclosure, the hole for the reference axis may be relatively small diameter compared to the lumen of the cannulated shaft 18. The reference axis hole may be drilled in the desired alignment using a reducer shaft 38. The reducer shaft 38 may be a cannulated shaft having an outside diameter sized to be received within the lumen of the cannulated shaft 18. The inside diameter of the lumen of the reducer shaft 38 may be sized to receive and align a pilot drill bit for drilling a reference axis hole having the desired diameter. Similar to the cannulated shaft 18, the reducer shaft 38 may include a cupped or conical proximal receptacle 40. The cupped or conical receptacle 40 may facilitate aligning instruments, tools, and/or other devices with the lumen of the reducer shaft 38, and/or inserting such instruments, tools, and/or other devices into the lumen of the reducer shaft 38.

With the locating hoop 12 and cannulated shaft 18 aligned and locked in a desired orientation relative to the articular surface 22, the reducer shaft 38 may be inserted into the lumen of the cannulated shaft 18 via the opening 24 in the rear of the tool support 14. The reducer shaft 38 may extend through at least a portion of the lumen of the cannulated shaft 18. According to one embodiment, the reducer shaft 38 may extend through the cannulated shaft 18 and contact the bone 20 or terminate proximate the surface of the bone 20. In such a configuration, the instruments, tools, etc., such as the pilot drill bit, may be fully supported up to the surface of the bone 20.

With the reducer shaft 38 in position within the lumen of the cannulated shaft 18, a guide pin 42 may be loaded through the opening 24 of the tool support 14 and into the lumen of the reducer shaft 38. Loading the guide pin 42 into the lumen of the reducer shaft may be facilitated by the cupped or conical receptacle 40 of the reducer shaft 38. The guide pin 42 may include a drill tip (not shown) or other cutting feature disposed on a distal end of the guide pin 42. The guide pin may be driven, e.g., by a drive motor or manual drive handle, from the rear portion 26 of the tool support 14. The depth of the hole may be gauged by observing penetration of the guide pin 42 through the articular surface 22 within the opening of the locating hoop 12. Alternatively, the separation between the tool support 14 and the locating hoop 12 may be known based on the configuration of the arm 16, locating hoop 12, and tool support 14. In one embodiment, the guide pin 42 may be provided having indicia representative of depth of penetration. The depth of the reference axis hole may be determined from the relationship between the guide pin 42 and at least one of the tool support 14, the reducer shaft 38 and the cannulated shaft 18, etc.

After the guide pin 42 has been drilled into and/or through the bone 20 in the above described manner, the guide pin 42 may be maintained extending into/through the bone and/or articular surface 22. The guide pin 42 extending at least partially into or through the bone 20 may provide a reference axis aligned through the reducer shaft 38. The guide pin 42 may be used locate subsequent operations and/or instruments relative to the reference axis. Once the guide pin 42 has been positioned in the hole through the bone 20, the reducer shaft 38 may be withdrawn from the lumen of the cannulated shaft 18. At least a portion of the guide pin 42 may remain in the hole extending into the bone 20. If the guide pin 42 is provided with a close fit with the hole, the guide pin 42 may be maintained in a desired alignment with the reference axis.

According to an alternative embodiment, a drill may be used to provide a hole extending into and/or through the bone 20. The reducer shaft 38 may be used to align and/or support the drill bit during the drilling operation. After the hole has been drilled extending into or through the bone 20, a guide pin 42 may be inserted extending into or through the hole to provide a reference axis, in a similar manner to the preceding description.

After the guide pin 42 has been positioned extending from the bone 20 in a desired position relative to the reference axis, a larger hole may be drilled into the bone for receiving a fixation and/or location element. Consistent with one embodiment, the hole for the fixation element may extend all of the way through the bone 20 and the articular surface 22. In other embodiments, however, the hole for the fixation element may extend only partially through the bone 20.

Figure 14:
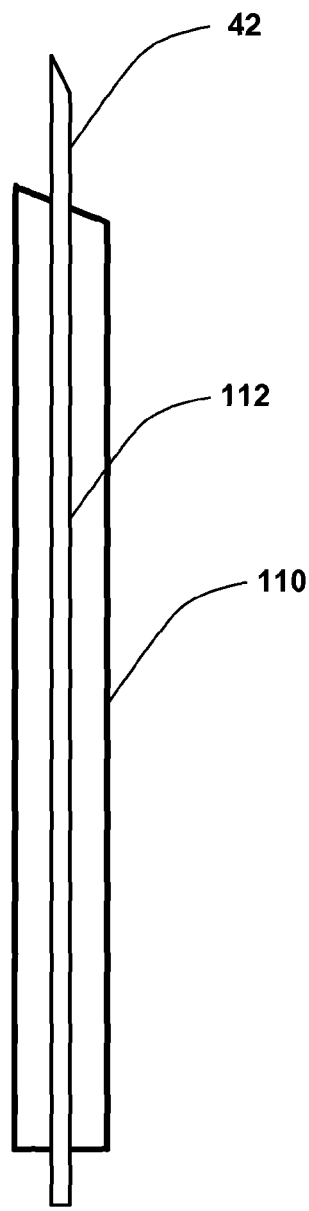
FIG. 14 is a cross-sectional view of one embodiment of a cored drill and a guide pin.
Figure 15:
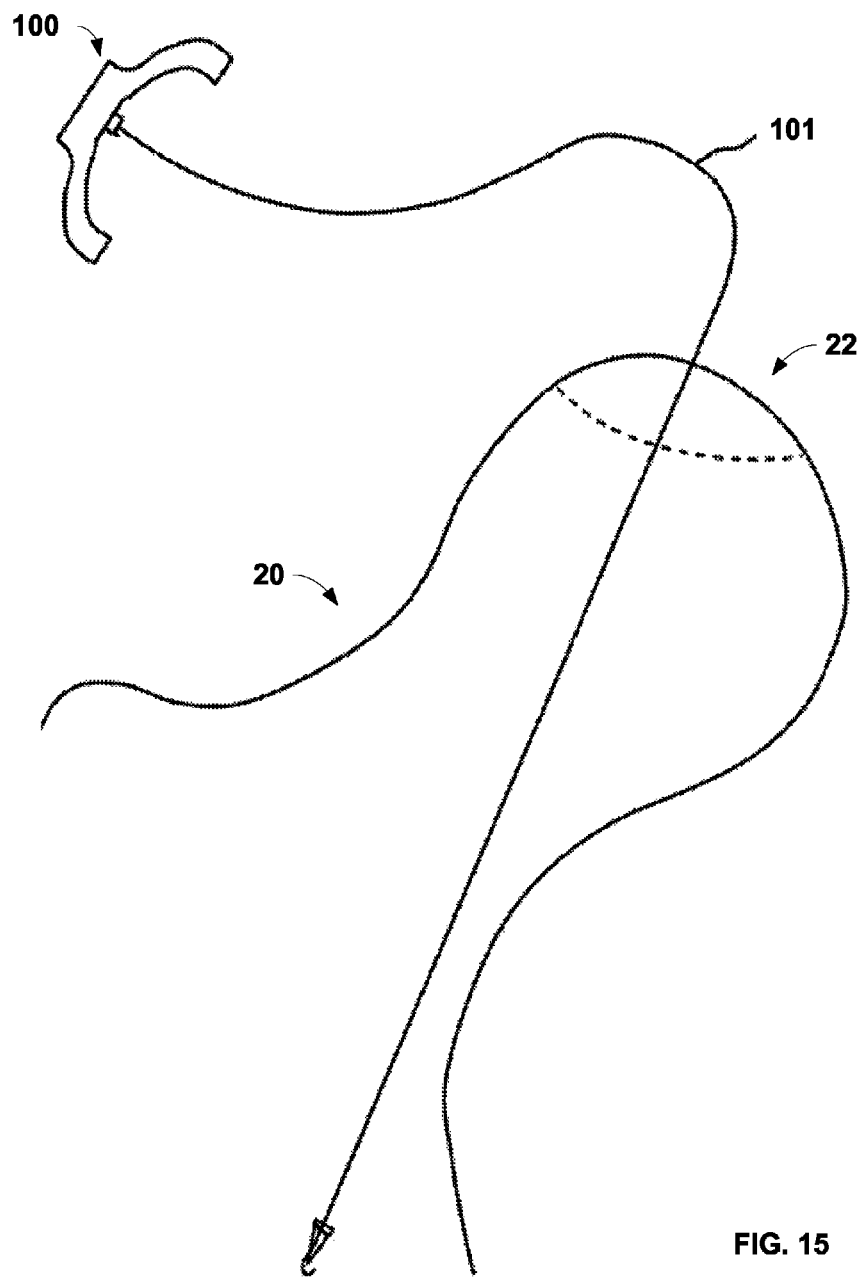
FIG. 15 is a cross-sectional view of one embodiment of a cutting device and a wire.

In one embodiment, the hole or tunnel for the fixation element may be drilled at least part of the way through the bone 20 using a cored drill 110, FIG. 14. That is, the drill 110 may include a lumen 112, or opening therethrough. The lumen 112 through the drill 110 may be sized to receive the guide pin 42. With the guide pin 42 received through the lumen 112 of the drill 110, the hole for the fixation element may be drilled into the bone 20 with the drill carried on/supported by the guide pin. Carrying the drill 110 on the guide pin 42 in this manner may allow the hole for the fixation element to be provided in a desired alignment relative to the reference axis through the articular surface 22. Additionally, carrying the drill 110 on the guide pin 42 may, for example, eliminate the need for an additional reducer tube to support the drill on the outside diameter thereof in a situation in which the outside diameter of the drill is less than the inside diameter of the lumen of the cannulated shaft 18. Alternatively, or additionally, a reducer tube supporting the outside diameter of the drill may be used for drilling the hole.

Figure 3:
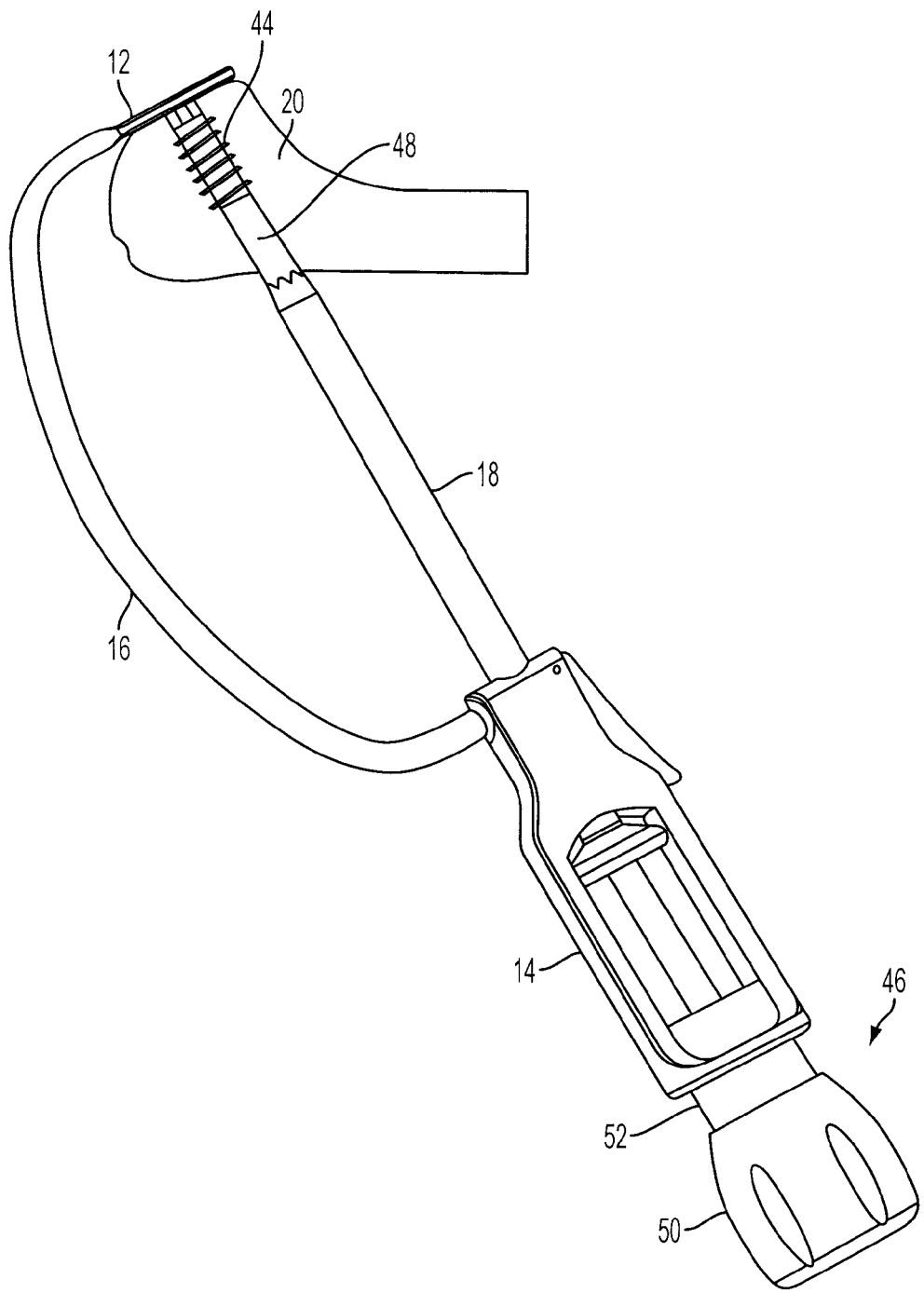
FIG. 3 shows a fixation element positioned below an articular surface using a retrograde articular surface replacement system according to the present disclosure.

Turning next to FIGS. 3 and 4, after a hole or tunnel has been drilled through the bone 20 for a fixation element, the fixation element may be positioned within the bone. Consistent herewith, the fixation element may be an element adapted to retain, or assist in retaining, an implant to the bone 20. In the illustrated embodiment, the fixation element is configured as a screw 44. According to one embodiment, the screw 44 may be delivered to the bone 20 through the cannulated shaft 18. The outside diameter of the screw 44 may, therefore, be smaller than the inside diameter of the lumen of the cannulated shaft 18, thereby allowing the screw to be passed from the tool support 14 and through the cannulated shaft 18. The hole through the bone 20 for receiving the screw 44 may have a diameter smaller than the outside diameter of the threads of the screw 44 to allow the threads of the screw 44 to engage the bone 20. Various other elements or features may additionally or alternatively be used as fixation elements.

Consistent with the illustrated embodiment, the screw 44 may be rotatably driven, i.e., screwed, into the bone using a probe-driver 46. The probe-driver 46 may include a shaft 48 that is configured to extend through the lumen of the cannulated shaft 18. A distal region of the shaft 48 may be provided having a feature for engaging and/or driving the screw 44. For example, the shaft 48 may include a hexagonal region that is adapted to be received by a corresponding hexagonal socket, or opening, in the screw 44. Various other features and configurations may be utilized to permit the shaft 48 to engage and/or drive the screw 44.

The probe-driver 46 may also include a knob 50 coupled to the proximal end of the shaft 48. The knob 50 may be coupled to the shaft 48 in a torsionally stiff manner such that rotating the knob 50 may also rotate the shaft 48 to drive the screw 44. Additionally, the probe-driver may include a cylindrical region 52 that may be sized to be rotatably received in the opening 24 of the tool support 14. According to one embodiment, the cylindrical region 52 may be sized relative to the opening 24 so that the probe-driver 46 may be supported by the opening 24 of the tool support 14.

Consistent with one embodiment, the cylindrical region 52 of the probe-driver 46 and the tool support 14 may include cooperating indicia (not shown) representative of the depth of penetration of the cylindrical region 52 into the opening 24 of the tool support 14. According to one embodiment, the indicia may be correlated to depth of insertion of the screw 44 into the bone 20. Accordingly, the depth of installation of the screw 44 into the bone 20 can be controlled and/or ascertained. The cooperating indicia may include, for example, a graduated scale and a reference, a vernier scale, or other system of reference marks.

Consistent with a particular embodiment, the indicia may be correlated to the depth of the screw 44 beneath the articular surface 22. Such a correlation may be achieved based on the known distance between the articular surface 22, as established by the locating hoop 12, and the tool support 14 which is established by the arm 16. Using a screw 44 having a known length and a predetermined seating height of the screw on the shaft 48 of the probe-driver 46, it may be possible to drive the screw 44 into the bone 20 to a predetermined distance from the articular surface 22.

Figure 5:
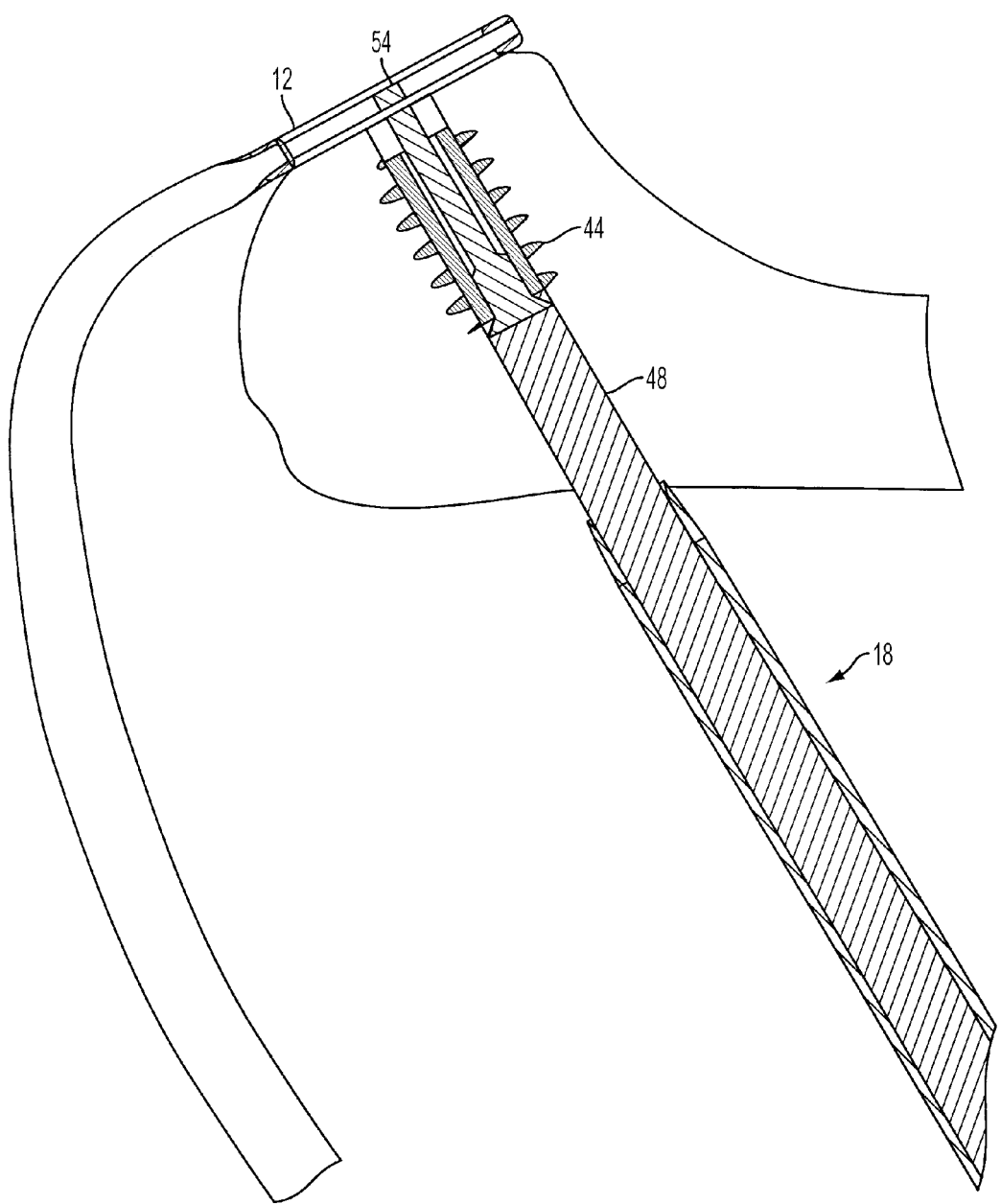
FIG. 5 is an enlarged cross-sectional view of a portion of the retrograde articular surface replacement system of FIG. 4 adjacent a locating hoop thereof.
Figure 6:
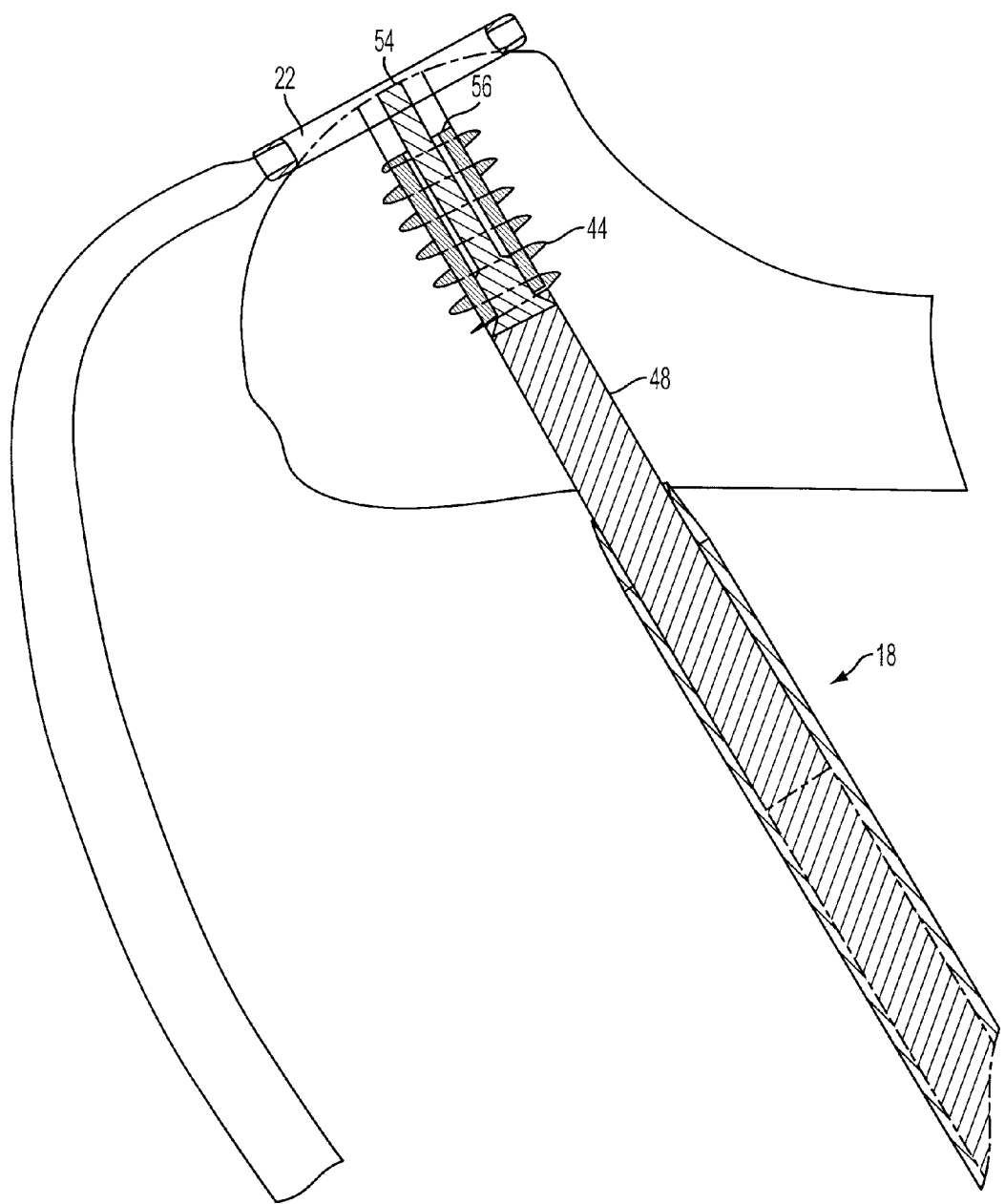
FIG. 6 is an enlarged cross-sectional view of a portion of a retrograde articular surface replacement system consistent with the present disclosure including a depth probe

With additional reference to FIGS. 5 and 6, the distal end of the shaft 48 may include a probe feature 54. As shown, the probe feature 54 may extend through the screw 44 and beyond the end of the screw 44 a predetermined distance. Consistent with the embodiment illustrated in FIG. 5, the probe feature 54 may be used to position the screw 44 at a predetermined depth in the bone 20 relative to the locating hoop 12. The screw 44 may be provided having a known length and may be configured to seat on the shaft 48 of the probe-driver 46 a known distance from the distal tip of the shaft 48. The known length and known seating height of the screw 44 may be based on predetermined design characteristics and/or on measurements taken prior to installation of the screw 44. Consistent with the embodiment of FIG. 5, the screw 44 may be positioned at a predetermined depth relative to the locating hoop 12 by driving the screw 44 until the probe feature 54 reaches a predetermined height relative to the locating hoop 12. For example, the screw 44 may be driven into the bone until the tip of the probe 54, at the distal end of the shaft 48 of the probe-driver 46, is flush with the top of the locating hoop 12 as shown. Various other alignment relationships between the tip of the probe 54 on the shaft 48 of the probe-driver 46 may also, or alternatively, be used for positioning the screw 44 at a desired depth within the bone 20.

In a related embodiment, illustrated in FIG. 6, the probe feature 54 of the probe-driver 46 may be used to position the screw 44 at a predetermined depth relative to the articular surface 22. For example, the screw 44 may be positioned at a predetermined depth relative to the original articular surface 22, or may be positioned at a predetermined depth relative to the articular surface 22 surrounding the hole for receiving the screw 44. According to either embodiment, a screw 44 may be provided having a predetermined length and having a predetermined seating height on the distal end of the shaft 48. The screw 44 may then be driven into the bone 20 until the probe feature 54 reaches a predetermined height relative to the articular surface 22.

Embodiments may be provided combining various aspects of the previously described cooperating indicia on the probe-driver 46 and tool support 14 and the probe feature 54 on the shaft 48 of the probe-driver 46. Such embodiments combining these aspects may be used to position the screw at a predetermined depth relative to at least one of the locating hoop 12 and the articular surface 22.

According to an alternative embodiment, the fixation element, such as screw 44 may be inserted into the bone from the articular surface 22. According to such an embodiment, after a hole has been drilled through the articular surface 22, the screw 44 may be passed to the articular surface 22 and introduced into the hole therein. For example, a line, such as a metal wire, plastic filament, etc., may be passed through the hole and the screw 44 or attached to the screw 44 and pass through the hole. The screw 44 may then be drawn to the hole in the articular surface 22. The screw 44 may then be driven into the articular surface in a manner similar to the preceding embodiment, e.g., using a drive shaft extending through the hole in the bone 20.

After the screw 44 has been installed at a desired position in the bone 20, a region of the articular surface 22 surrounding the axis of the screw 44 may be excised to provide an implant site. The articular surface 22 may be excised using a rotating cutting device 100, FIG. 14, that may be positioned so that the rotational axis of the cutting device 100 may be generally aligned with the axis of the opening through the screw 44 (screw 44 not shown in FIG. 14 for clarity). According to one embodiment, a line 101, such as a metal wire, plastic filament, etc., may be passed through the bone 20 so that it extends from the articular surface 22 and from the opposed side of the bone. The wire 101 may pass through, or be coupled to the cutting device 100 along the rotational axis there of. The cutting device 100 may then be drawn toward the articular surface 22 by withdrawing the wire 101 through the bone or by sliding the cutting device 100 along the wire 101 towards the articular surface 22. In either case, the wire 101 passing through the bone 20 may act to align the rotational axis of the cutting device 100 with the axis of the opening through the screw 44. Alternative methods for positioning the cutting device 100 relative to the articular surface 22 may also be employed consistent with the present disclosure, including manually positioning the cutting device 100.

According to one embodiment, the cutting device may include a socket or opening along the rotational axis of the cutting device. For example, the cutting device may include a hexagonal socket along the rotational axis of the cutting device. The socket or opening along the rotational axis of the cutting device may allow the cutting device to be rotationally driven to excise at least a portion of the articular surface. Once the cutting device has been positioned on the articular surface with the rotational axis of the cutting device generally aligned with the opening through the screw 44, a drive shaft may be inserted through the hole through the bone and the opening through the screw and may engage the cutting device. For example, in the case of a cutting device having a hexagonal socket, the drive shaft may include a hexagonal feature adapted to be received in the hexagonal socket of the cutting device.

Once the drive shaft has been engaged with the cutting device, the cutting device may be rotatably driven by the drive shaft. The drive shaft, and thereby the cutting device, may be manually driven, e.g., by rotating a handle proximal to the cutting device, or may be mechanically drive, e.g., by a drive motor or drill device. While the cutting device is being rotatably driven by the drive shaft, the cutting device may also be pulled in to the articular surface 22, thereby excising the articular surface to form a generally circular implant site.

The depth of the implant site may be controlled in a variety of manners including visual inspection of the implant site and/or the depth of the cutting device in the implant site, indicia on the drive shaft indicative of the depth the cutting device has been pulled into the articular surface, etc. According to one embodiment, the depth of the implant site may be controlled by the screw 44, or other fixation element. The screw 44 may include an upper bearing surface 56, generally in FIG. 6. The cutting device may have a corresponding lower bearing surface adjacent the screw 44. The cutting device may be rotatably driven and pulled into the articular surface 22 until the lower bearing surface of the cutting device bears against the upper bearing surface 56 of the screw 44. Accordingly, the excision site may be provided having a predetermined depth relative to the screw.

Depending upon the diameter of the implant site, the locating hoop 12 and/or the tool support 14 may be removed from the bone 20 prior to excising the implant site. For example, if the diameter of the implant site is to be equal to, or greater than, the inside diameter of the locating hoop 12, it may be desirable to remove the locating hoop from the region of the articular surface 22 to be excised prior to excising the implant site. If the diameter of the implant site, however, is to be smaller than the inside diameter of the locating hoop 12, the locating hoop 12 may optionally be maintained in position on the articular surface 22. If the locating hoop 12, tool support 14, etc., are removed during excision of the implant site, the opening extending through the screw 44 may serve as an alignment feature. That is, the diameter of the drive shaft may be dimensioned relative to the opening through the screw 44 such that the drive shaft may be maintained in a generally desired alignment by the opening through the screw 44 during excision of the implant site.

According to an alternative embodiment, the implant site may be excised prior to, or without, the installation of a fixation element such as a screw. In such an embodiment, the depth of the implant site may be provided using visual inspection, indicia on the drive shaft and/or cutting device, etc. The orientation of the excision may be controlled either by the tool support 14, e.g. via a guiding cannulated shaft or other guide feature, or by the hole through the bone. In either case the implant site may be provided in a manner as described above, with the cutting device being rotatably driven to excise a desired portion of the articular surface 22, and/or underlying bone 20.

Figure 7:
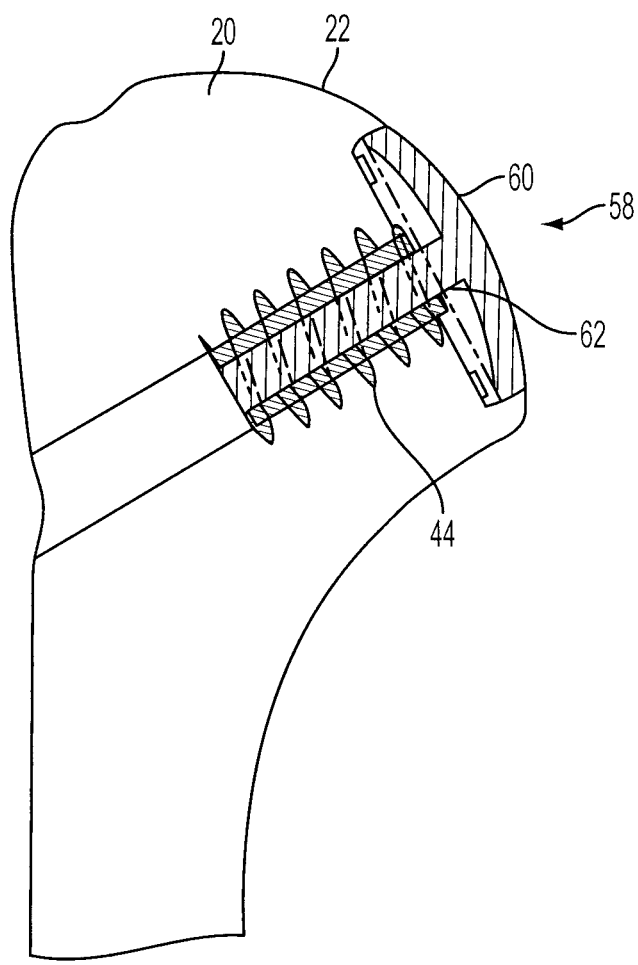
FIG. 7 is a representational cross-sectional view of an articular surface having an implant installed therein using a retrograde articular surface replacement system according to the present disclosure.

As shown in FIG. 7, once the implant site has been excised, an implant 58 replacing at least a portion of the articular surface 22 may be installed into the implant site. A wide variety of implants and/or implants having various different characteristics may suitable be employed to replace at least a portion of an articular surface consistent with the present disclosure. Accordingly, the disclosure herein should not be considered to be limited to a particular implant. According to one embodiment, a suitable implant may have a generally circular shape. However, implants having various other shapes may also be required depending upon the shape of the implant site. Implant sites having a non-circular shape may result when at least a portion of the cutting path of the cutting device does not contact the articular surface or bone. For example, if at the depth of the implant site the width of the articular surface is less than the cutting radius of the cutting device, an implant site may be provided having a truncated circular shape. Various other shapes of implant sites may result depending upon the profile of the articular surface at the depth of the implant and the radius of the cutting path of the cutting device used to excise the implant site.

Referring again to FIG. 7, an implant 58 according to the illustrated embodiment of the present disclosure may be provided having a load bearing surface 60 that may approximate the geometry or curvature of the articular surface being replaced by the implant. In one embodiment the geometry of the load bearing surface may be based on the actual articular surface being replaced. For example, mapping techniques known in the art may be used to measure the geometry of the region of the actual articular surface being replaced. An implant may then be constructed or selected from a set of implants having predetermined geometries. Alternatively, an implant for a specific application may be fabricated or selected from a set of standard sized/shaped implants to provide a general approximation of the articular surface being replaced. Selection or fabrication of an implant may rely on various degrees of quantitative reference to the articular surface being replaced, including no quantitative reference to the articular surface.

According to one aspect, the system herein may be used to provide information regarding the curvature of the articular surface 22. According to one embodiment, the curvature of the articular surface 22 may be measured or approximated using the locating hoop 12. The locating hoop 12 may contact the articular surface at a plurality of locations about the bottom circumference of the locating hoop 12 and/or continuously about the bottom circumference of the locating hoop 12. The height of the articular surface 22 in the center of the locating hoop 12 may be measured relative to the bottom circumference of the locating hoop 12, for example by using the probe-driver 46. Two generally opposed points of contact between the bottom circumference of the locating hoop 12 together with the radius of the locating hoop 12, and the height of the articular surface 22 generally in the center of the locating hoop 12 may define three points on a curve generally corresponding to the curvature of the articular surface. The geometry of the articular surface 22 may be mapped or approximated by developing one or more such curves approximating the curvature of the articular surface. A map or approximation of the curvature of the articular surface 22 may be used to select and/or fabricate an implant that may suitably replace a desired portion of the articular surface 22.

An implant 58 may be retained in an implant site by a variety of mechanisms. For example, the implant may include one or more features adapted to interact with the fixation element to retain the implant in the implant site. Consistent with the illustrated embodiment, the screw 44 may include an opening extending there through. At least a portion of the opening may be configured having a precision taper. The implant 58 may include a post 62 having a precision taper adapted to mate with the taper of the opening of the screw 44. The implant 58 may be retained in the implant site by inserting the tapered post 62 of the implant 58 into the tapered opening in the screw 44 and applying an axial pressure or impact to the implant 58, thereby seating the tapered post 62 in the tapered opening.

Various other features and methods may be used to retain the implant in the implant site. The implant and the fixation element may include interacting or cooperating features other than a tapered post and tapered opening. For example, the fixation element and implant may include conventional compression fits features, snap-fits, etc. In an embodiment that does not employ a separate fixation element, the implant may include a feature such as a barbed post that may engage the sides of the implant site and/or a hole drilled into, or through, the bone. Bone cement may additionally, or alternatively, be used to secure an implant in an implant site.

According to a related embodiment, the locating hoop 12 and tool support 14 may be removed after the guide pin 42 has been installed in the bone 20. As discussed above, the guide pin 42 may establish a reference axis for carrying out subsequent steps of an articular surface replacement procedure. For example, the guide pin may establish a reference axis for guiding a cored drill bit, described above. The cored drill may be used to provide a tunnel for a fixation element which may include an opening or a feature oriented in a predetermined relationship to the reference axis. According to one embodiment, the opening or feature in the fixation element may be used for positioning and aligning subsequent operations, instruments, and/or devices.

Figure 8:
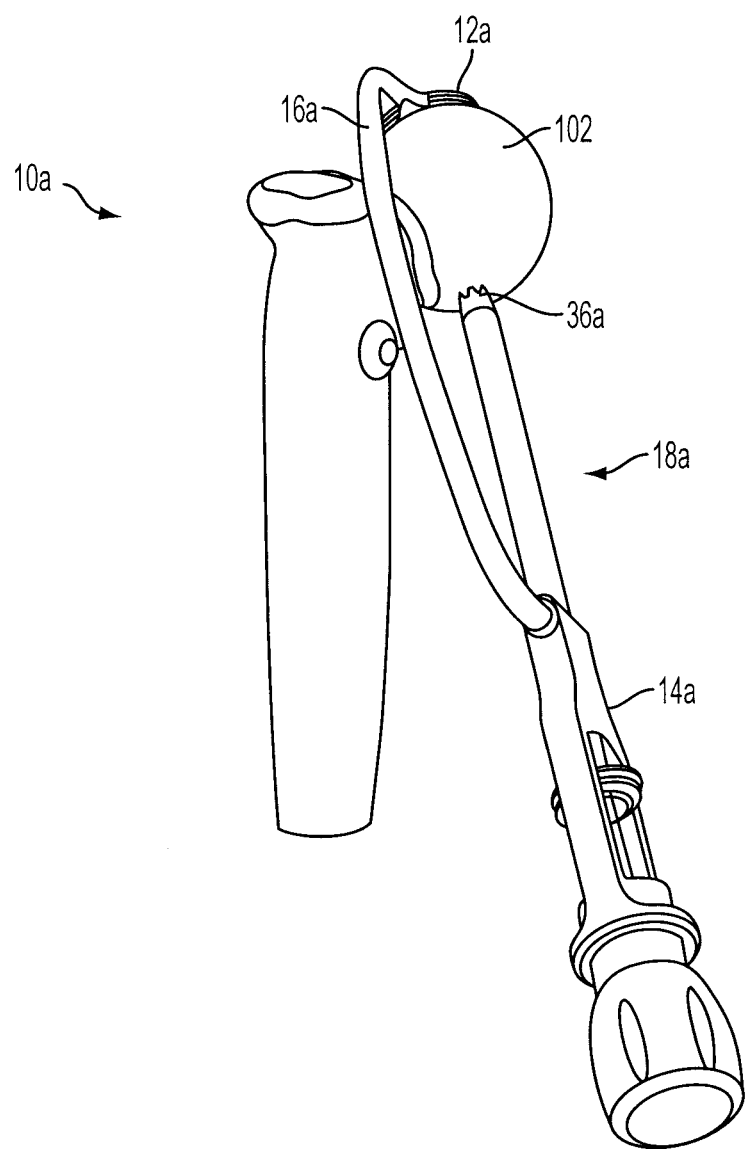
FIG. 8 is a perspective view of a retrograde articular surface replacement system consistent with the present disclosure applied to an articular surface of a femoral head.
Figure 9:
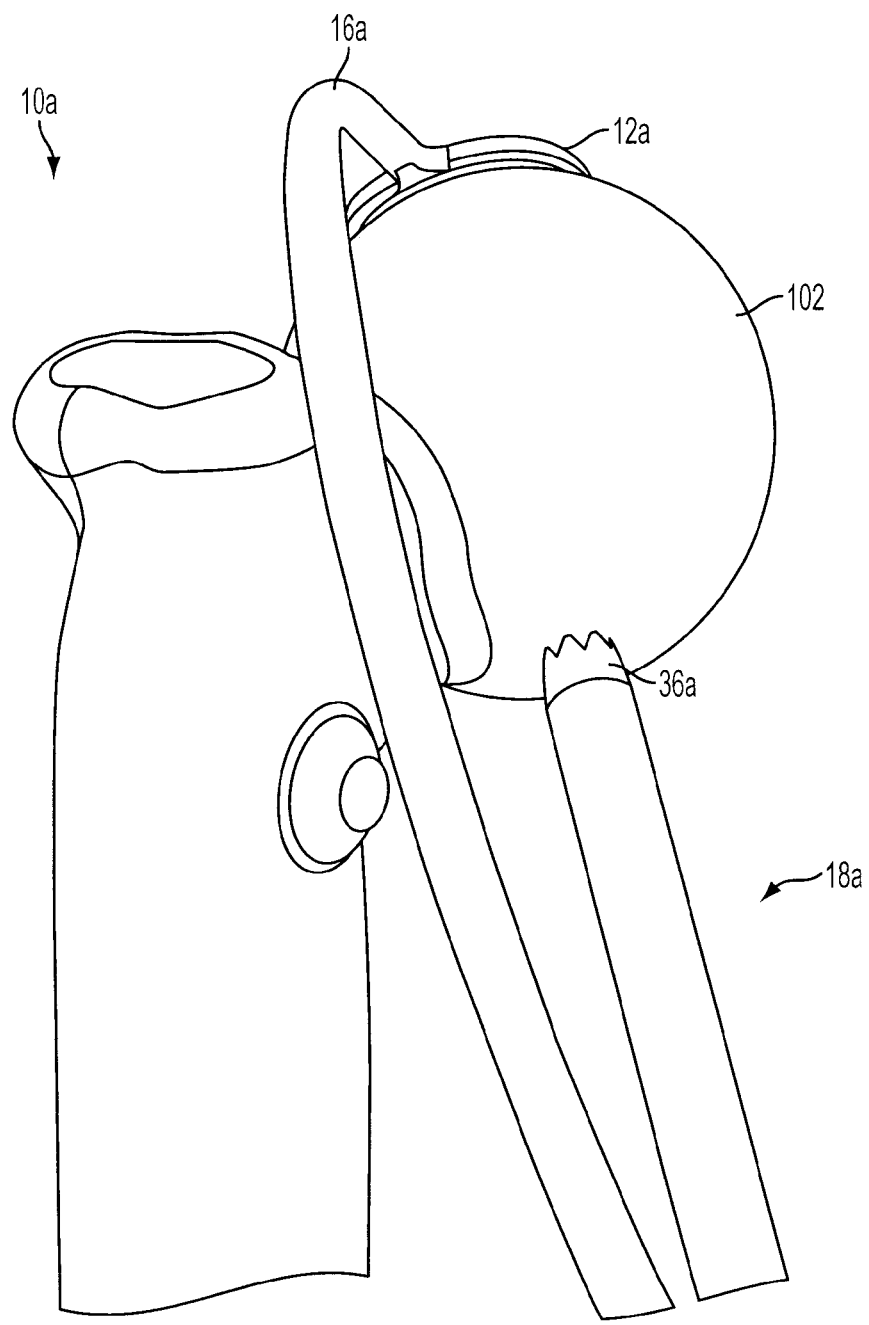
FIG. 9 is an enlarged view of a portion of the articular surface replacement system of FIG. 8 adjacent the articular surface of the femoral head.

Turning to FIGS. 8 and 9, the versatility of an articular surface replacement system 10a is illustrated. In the depicted embodiment the articular surface replacement system 10a is shown positioned to replace at least a portion of an articular feature such as femoral head 102. As with the previously described embodiment, the system 10a may generally include a locating hoop 12a coupled in a predetermined orientation and alignment with a tool support 14a by an arm 16a. The tool support 14a may, in turn, position a cannulated shaft 18a in a predetermined orientation and alignment with the locating hoop 12a.

Consistent with the illustrated embodiment, the biting features of the distal tip 36a of the cannulated shaft 18a may be especially useful for reducing or preventing undesired movement of the cannulated shaft 18a relative to the femoral head 102, or a similar highly arcuate or angled surface. As also indicated in the illustrated embodiment, the articular replacement system 10a may suitably be employed to replace a portion of a femoral head 102, or similarly configured joint, without reference to the axis of the neck of the joint. This aspect of the present disclosure may allow the amount of the articular surface being replaced to be minimized.

Referring to FIGS. 10 through 13, a further embodiment of the articular surface replacement system is illustrated. In the further embodiment, an articular surface replacement system consistent with the present disclosure may be used to access an articular surface, at least in part, by tunneling through an adjacent bone. In the illustrated embodiment, a portion of a glenoid articular surface 62 may be accessed through a portion of the humerus 20a and the articular surface 22 thereof. For the purpose of clarity and the ease of understanding, the glenoid articular surface 62 and surrounding structure are only representationally depicted in a simplified manner, rather than being illustrated in the full and complete structure of the scapula. Similarly, the structure and relationship of the humerus and glenoid also representationally depicted, in an at least slightly exploded form, for the sake of clarity and illustration of detail. While the illustrated embodiment is depicted with reference to the head of the humerus and the glenoid articular surface, the system herein is susceptible to use in the context of various other bones, joints, and articular surfaces.

Figure 10:
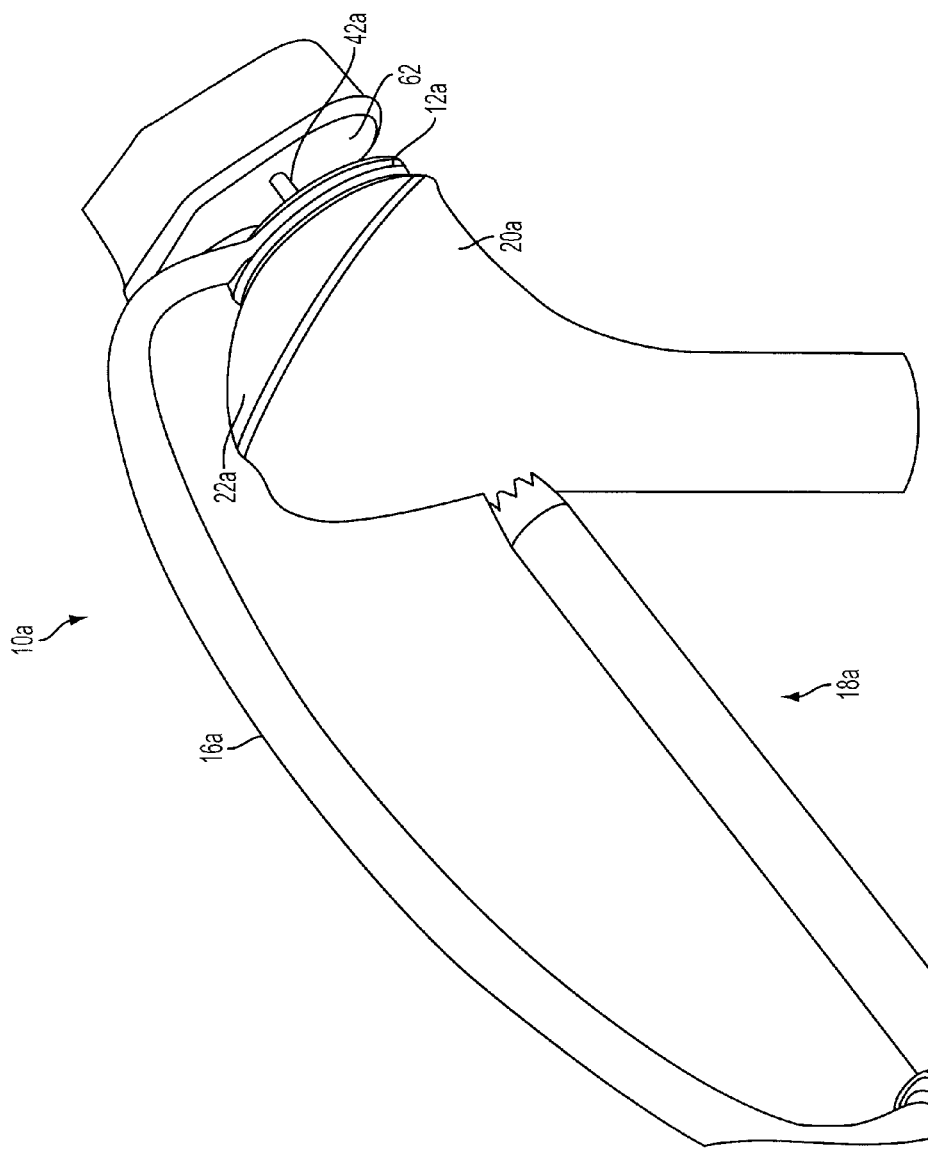
FIG. 10 is a perspective view of an embodiment of the articular surface replacement system in use to replace a cooperating articular surface consistent with the present disclosure.

Referring first to FIG. 10, the system 10a, generally including a locating hoop 12a coupled to a tool holder (not shown) via an arm 16a may be used to locate a cannulated shaft 18a in a desired relationship to defect on the articular surface 22a of the humerus 20a, or on the glenoid articular surface 62 in a manner generally as described with reference to the preceding embodiment. Particularly, the locating hoop 12a may be located surrounding, or in a desired relationship to, a defect in, or portion of, the articular surface to be replaced. Consistent with the illustrated embodiment, the defect or portion to be replaced may be located in either the articular surface 22a of the humerus or in the glenoid articular surface 62. Consistent with an embodiment herein, a corresponding portion of each articular surface 22a, 62 may be replaced.

As shown, with the locating hoop 12a located in a desired relationship to the defect or portion of an articular surface 62 to be replaced, a guide pin 42a may be drilled through the humerus 20a an the articular surface 22a thereof, using a cannulated shaft 18a to orient and support the guide pin 42a. The guide pin 42a may provide a reference axis for carrying out subsequent procedures. According to one embodiment, the guide pin 42a may be drilled at least a portion of the way into the glenoid articular surface 62 to mark the point of intersection of the reference axis with the glenoid articular surface 62.

Figure 11:
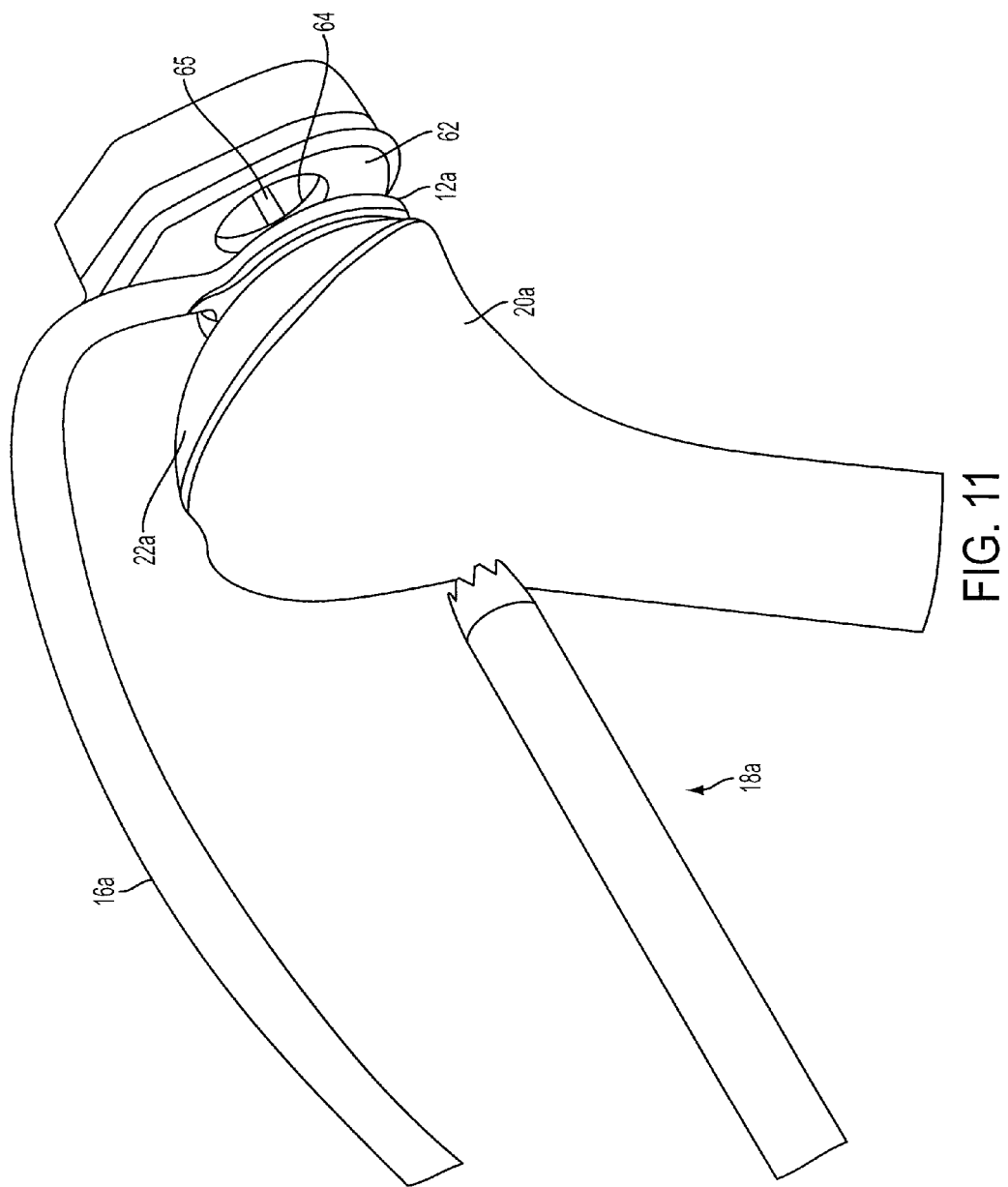
FIG. 11 illustrates an implant site excised in a cooperating articular surface consistent with the present disclosure.

Turning next to FIG. 11, after a reference axis has been provided through the humerus 20a, an implant site 64 may be created in the glenoid articular surface 62. The implant site 64 may be provided by supplying a rotary cutter between the glenoid articular surface 62 and the articular surface 22a of the humerus 20a. The rotary cutter may include a socket or opening for receiving a drive shaft 65 therein. The drive shaft 65 may be provided extending through the humerus 20a and may rotatably engage the rotary cutter between the articular surface 22a of the humerus 20a and the glenoid articular surface 62. The rotary cutter may be manually or mechanically rotatably driven and urged into the glenoid articular surface 62 to excise a region of the glenoid articular surface 62 and underlying bone. As would be expected, the rotary cutter may produce an implant site 64 in the glenoid articular surface 62 having a generally circular geometry.

Figure 12:
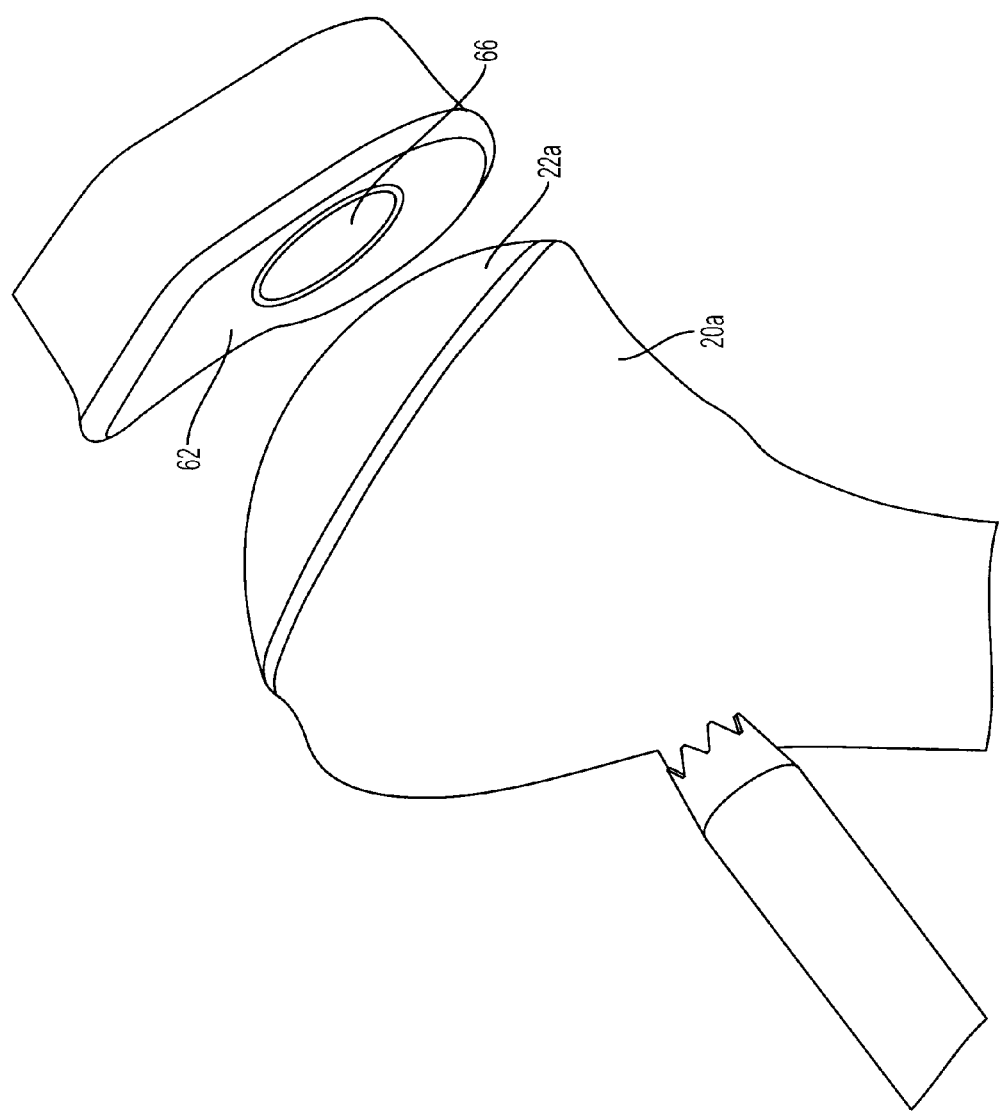
FIG. 12 depicts an articular surface implant installed in a cooperating articular surface.
Figure 13:
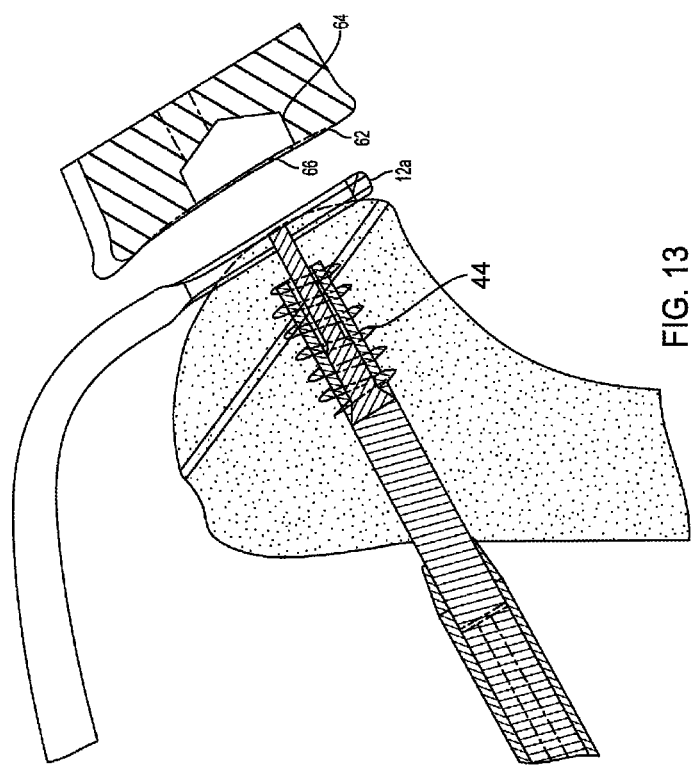
FIG. 13 is a cross-sectional view of the articular surface of FIG. 12.

Referring to FIGS. 12 and 13, after the implant site 64 has been excised, an implant 66 may be installed therein. Consistent with the illustrated embodiment, the implant 66 may have a generally circular cross-section and may have an outward face that may replace the excised region of the glenoid articular surface 62. The outward face of the implant 66 may be provided to generally correspond to the original glenoid articular surface 62, based on varying degrees of quantitative and/or qualitative comparison. Alternatively, or additionally, the implant 66 may have an outward face that is adapted to provide a desired interaction with a cooperating implant to be installed in the articular surface 22a or the humerus 20a. The implant 66 may be installed in the implant site 64 using a variety of techniques, including bone cement, separate fixation elements, one or more features on the implant to engage the walls of the excise site, etc., including combination thereof.

An implant site may be created in the articular surface 22a of the humerus 20a to provide an implant in the articular surface 22a of the humerus 20a that may interact with the implant 66 in the glenoid articular surface 62. Such an implant site may be created as described with reference to FIGS. 1 through 7. The implant site in the humerus 20a may be provided either before or after the implant site 64 in the glenoid articular surface 62.

Various other features and advantages of the articular replacement system described herein will be appreciated by those having skill in the art. Similarly, the system disclosed herein is susceptible to numerous modifications and variations without materially departing from the spirit of the disclosure.

What is claimed is:

1. A method for replacing a portion of an articular surface comprising:
    forming a passage through a first bone behind a first articular surface, said passage extending toward said first articular surface;
    advancing a cannulated lumen within said passage until a portion of said cannulated lumen is disposed a predetermined depth beneath said first articular surface; and
    advancing a rotary cutter to excise an implant site on said first articular surface relative to said passage until a portion of said rotary cutter contacts said portion of said cannulated lumen.

2. A method according to claim 1, wherein forming said passage through bone behind said first articular surface comprises establishing a reference axis extending through said first articular surface.

3. A method according to claim 2, wherein said reference axis intersects said portion of said first articular surface.

4. A method according to claim 2, wherein establishing said reference axis comprises inserting a guide pin extending at least partially into said first bone.

5. A method according to claim 4, wherein forming said passage comprises drilling over said guide pin with a cored drill.

6. A method according to claim 2, wherein said implant site extends radially around said reference axis.

7. A method according to claim 6, wherein excising said implant site comprises rotating a cutter about said reference axis.

8. A method according to claim 1, wherein advancing said cannulated lumen includes installing a threaded element at least partially into said passage, said threaded element having an opening extending therethrough defining said lumen.

9. A method according to claim 8, wherein a depth of said implant site is controlled relative to an upper bearing surface of said threaded element.

10. A method according to claim 1, further comprising installing an implant into said implant site.

11. A method of claim 1, wherein advancing said rotary cutter to excise said implant site further comprises advancing said rotary cutter in a retrograde manner.

12. A method of claim 11, wherein said rotary cutter is coupled to a drive shaft configured to be received within said cannulated lumen.

13. A method of claim 12, wherein said drive shaft and said cannulated lumen are configured to maintain said drive shaft in a desired alignment during excision of said implant site.

14. A method of claim 1, wherein said cannulated lumen includes a screw.

15. A method of claim 1, further comprising securing an implant to said cannulated lumen.

16. A method of claim 15, wherein securing said implant to said cannulated lumen includes advancing a tapered post of said implant into a corresponding tapered portion of said cannulated lumen.

17. A method of claim 16, wherein advancing said tapered post of said implant into said corresponding tapered portion of said cannulated lumen further includes applying an axial pressure to said implant.

18. A method of claim 1, wherein said cannulated lumen includes a fixation element.

19. A method of claim 1, further comprising accessing a second articular surface of a second bone through said passage, said second articular surface facing said first articular surface.

\* \* \* \* \*

UNITED STATES PATENT AND TRADEMARK OFFICE
CERTIFICATE OF CORRECTION

PATENT NO. : 8,556,902 B2
APPLICATION NO. : 13/043430
DATED : October 15, 2013
INVENTOR(S) : Steven W. Ek et al.

It is certified that error appears in the above-identified patent and that said Letters Patent is hereby corrected as shown below:

Title Page

On page 1, column 1, item (75), Inventors, line 1, delete "Tim" and insert -- "Timothy", -- therefor.

On page 1, column 2, item (57), Abstract, line 5, delete "though," and insert -- through, -- therefor.

On page 7, column 2, item (56), Other Publications, line 62, delete "patnet" and insert -- patent -- therefor.

On page 7, column 2, item (56), Other Publications, line 64, delete "patnet" and insert -- patent -- therefor.

On page 7, column 2, item (56), Other Publications, line 66, delete "patnet" and insert -- patent -- therefor.

On page 7, column 2, item (56), Other Publications, line 68, delete "patnet" and insert -- patent -- therefor.

On page 9, column 1, item (56), Other Publications, line 4, delete "Jorunal" and insert -- Journal -- therefor.

On page 9, column 1, item (56), Other Publications, line 19, delete "Experimantal" and insert -- Experimental -- therefor.

On page 9, column 1, item (56), Other Publications, line 29, delete "Experriences" and insert -- Experiences-- therefor.

On page 9, column 1, item (56), Other Publications, line 49, delete "Medicing" and insert -- Medicine -- therefor.

Signed and Sealed this
Twenty-eighth Day of January, 2014

Michelle K. Lee
*Deputy Director of the United States Patent and Trademark Office*

CERTIFICATE OF CORRECTION (continued)
U.S. Pat. No. 8,556,902 B2

On page 9, column 1, item (56), Other Publications, line 49, delete "Natinal" and insert
-- National -- therefor.

On page 10, column 1, item (56), Other Publications, line 29, delete "Nonarthoplasty" and insert
-- Nonarthroplasty -- therefor.

On page 10, column 2, item (56), Other Publications, line 27, delete "Repoort" and insert
-- Report -- therefor.